(12) United States Patent
Mustelin et al.

(10) Patent No.: US 8,188,080 B2
(45) Date of Patent: May 29, 2012

(54) VHR PROTEIN TYROSINE PHOSPHATASE INHIBITORS, COMPOSITIONS AND METHODS OF USE

(75) Inventors: Tomas Mustelin, La Jolla, CA (US); Lutz Tautz, La Jolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 746 days.

(21) Appl. No.: 12/253,804

(22) Filed: Oct. 17, 2008

(65) Prior Publication Data
US 2009/0105254 A1    Apr. 23, 2009

Related U.S. Application Data

(60) Provisional application No. 60/999,300, filed on Oct. 17, 2007.

(51) Int. Cl.
*A61K 31/535* (2006.01)
*C07D 277/00* (2006.01)

(52) U.S. Cl. ........................ 514/236.5; 514/369; 548/183

(58) Field of Classification Search ................ 514/236.5, 514/369; 548/183
See application file for complete search history.

(56) References Cited

U.S. PATENT DOCUMENTS
7,402,602 B2 *    7/2008    Bigg et al. .................... 514/396

OTHER PUBLICATIONS

Suto et al. CAS: 142:176827, 2005.*
Bao et al. CAS: 141:376382, 2004.*
Klein et al. CAS: 140: 89899, 2004.*
McKee et al. CAS: 139:240341, 2003.*
McKee et al. CAS: 139:240337, 2003.*
Alonso, A. et al., (2003) Tyrosine phosphorylation of VHR phosphatase by ZAP-70. *Nat Immunol.* 4, 44-8.
Alonso, A. et al., (2001) Inhibitory role for dual specificity phosphatase VHR in T cell antigen receptor and CD28-induced Erk and Jnk activation. *J Biol Chem* 276, 4766-71.
Canagarajah, B. J. et al., (1997) Activation mechanism of MAP kinase ERK2 by dual phosphorylation. *Cell* 90, 859-69.
Chau, A. S. et al., (1999) Inactivation of p42 mitogen-activated protein kinase is required for exit from M-phase after cyclin destruction. *J Biol Chem* 274, 32085-90.
De Luca, L. et al., A Mild Procedure for the Preparation of 3-aryl-4-formylpyrazoles, *Synlett* 2004, No. 13, pp. 2299-2302.
Grosch, S. et al., (2003) Activation of c-Jun-N-terminal-kinase is crucial for the induction of a cell cycle arrest in human colon carcinoma cells caused by flurbiprofen enatiomers. *Faseb J* 17, 1316-8.
Hamaguchi, T. et al., (1995) Rk-682, a potent inhibitor of tyrosine phosphatase, arrested the mammalian cell cycle progression at G1 phase. *FEBS Lett.* 372, 54-58.
Ip, Y. T. et al., (1998) Signal transduction by the c-Jun N-terminal kinase (JNK)-from inflammation to development. *Curr Opin Cell Biol* 10, 205-19.

Ishibashi, T. et al., (1992) Expression cloning of a human dual-specificity phosphatase. *Proc Natl Acad Sci USA* 89, 12170-4.
Ishida, K. et al., (2004) Exploitation of heparanase inhibitors from microbial metabolites using an efficient visual screening system. *J Antibiot.* 57, 136-42.
Pumiglia, K. M. et al., (1997) Cell cycle arrest mediated by the MEK/mitogen-activaed protein kinase pathway. *Proc Natl Acad Sci USA* 94, 4448-52.
Rahmouni, S. et al., (2006) Loss of VHR causes cell-cycle arrest and senescence. *Nat Cell Biol.* 8, 524-531.
Robinson, M. J. et al., (1997) Mitogen-activated protein kinase pathways. *Curr Opin Cell Biol* 9, 180-6.
Roggo, B.E. et al., (1994) 3-alkanoyl-5-hydroxymethyl tetronic acid homologues and resistomycin: new inhibitors of HIV-1 protease. I. Fermentation, isolation and biological activity. *J Antibiot.* (Tokyo) 47, 136-42.
Roggo, B.E. et al., (1994) 3-alkanoyl-5-hydroxymethyl tetronic acid homologues: new inhibitors of HIV-1 protease. II. Structure determination. *J. Antibiot.* (Tokyo) 47, 143-7.
Serrano, M. et al., (1997) Oncogenic ras provokes premature cell senescence associated with accumulation of p53 and p16INK4a. *Cell* 88, 593-602.
Sewing, A. et al., (1997) High-intensity Raf signal causes cell cycle arrest mediated by p21Cip1. *Mol Cell Biol* 17, 5588-97.
Shinagawa, S. et al., (1993) Tetronic acid derivatives, its manufacturing methods and uses. Japan. Kokai Tokyo Koho, JP 05-43568, 1-26.
Stein, G. H. et al., (1991) Senescent cells fail to express cdc2, cycA, and cycB in response to mitogen stimulation. *Proc Natl Acad Sci USA* 88, 11012-6.
Tautz, L. et al., (2006) Targeting the PTPome in human disease. *Ex. Op Ther Tar*, 10, 157-177.
Tchou, W.W. et al., (1999) Role of c-Jun N-terminal kinase 1 (JNK-1) in cell cycle checkpoint activated by the protease inhibitor N-acetyl-leucinyl-leucinyl-norleucinal. *Oncogene* 18, 6974-80.
Todd, J.L. et al., (2002) Dual-specificity protein tyrosine phosphatase VHR down-regulates c-Jun N-terminal knase (NK), *Oncogene* 21, 2573-83.
Todd, J.L. et al., (1999) Extracellular regulated kinases (ERK) 1 and ERK2 are authentic substrates for the dual-specificity protein-tyrosine phosphatase VHR. A novel role in down-regulating the ERK pathway. *J Bio Chem* 274, 13271-80.
Wang, W. et al. (2002) Sequential activation of the MEK-extracellular signal-regulated kinase and MKK3/6-p38 mitogen-activated protein kinase pathways mediates oncogenic ras-induced premature senescence. *Mol Cell Biol*22, 3389-403.
Waskiewicz, A. J. et al., (1995)Mitogen and stress response pathways: MAP kinase cascades and phosphatase regulation in mammals and yeast. *Curr Opin Cell Bio* 7, 798-805.
Woods, D. et al., (1997) Raf-induced proliferation or cell cycle arrest is determined by the level of Raf activity with arrest mediated by p21 Cip1. *Mol Cell Biol* 17, 5598-611.
Xue, Y. et al., (2003) Association of JNK1 with p21waf1 and p53: modulation of JNK1 activity. *Mol Carcinog* 36, 38-44.
Yuvniyama, J. et al., (1996) Crystal structure of the dual specificity protein phosphatase VHR, *Science* 172, 1328-31.

\* cited by examiner

*Primary Examiner* — Rei-tsang Shiao
(74) *Attorney, Agent, or Firm* — Pabst Patent Group LLP

(57) ABSTRACT

Disclosed herein are *Vaccinia* H1-related (VHR) protein tyrosine phosphatase (PTP) inhibitors that provide a method for treating cancer.

35 Claims, 1 Drawing Sheet

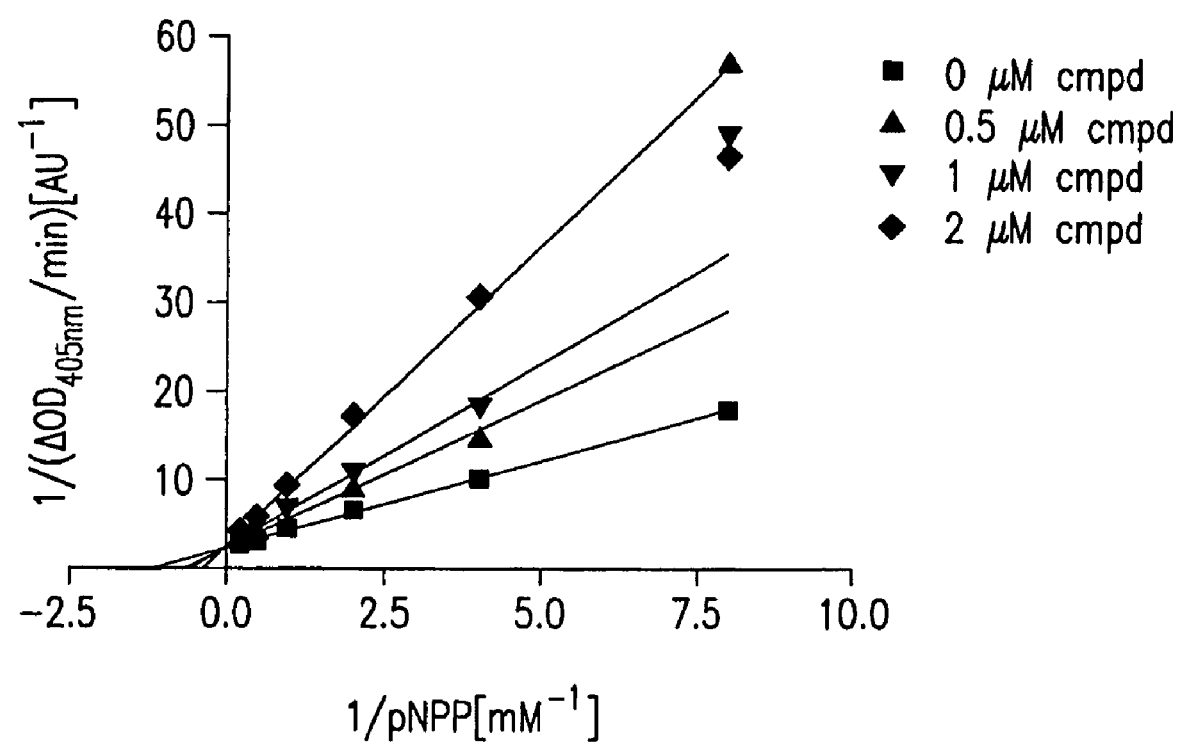

VHR PROTEIN TYROSINE PHOSPHATASE INHIBITORS, COMPOSITIONS AND METHODS OF USE

CROSS-REFERENCE TO RELATED APPLICATIONS

This application claims benefit of U.S. Provisional Application No. 60/999,300, filed Oct. 17, 2007. Application No. 60/999,300, filed Oct. 17, 2007, is hereby incorporated herein by reference in its entirety.

STATEMENT REGARDING FEDERALLY SPONSORED RESEARCH

This invention was made with government support under Grant R01 A1 35603 awarded by the National Institute of Health. The government has certain rights in the invention.

FIELD OF THE DISCLOSURE

The present disclosure relates to *Vaccinia* H1-related (VHR) protein tyrosine phosphatase (PTP) inhibitor compounds that can be used for treating cancer.

BACKGROUND

Protein tyrosine phosphatases (PTP's) are a class of enzymes, which just recently have been linked to various diseases including cancer, cardiovascular, immunological, infectious, neurological, and metabolic diseases (Tautz, L. et al., (2006) Targeting the PTPome in human disease. *Ex. Op Ther Tar,* 10, 157-177). *Vaccinia* H1-related (VHR) phosphatase is a dual-specificity phosphatase, which was cloned on the basis of sequence homology with the first identified dual-specificity protein phosphatase, the *Vaccinia* virus H1 open reading frame (Ishibashi, T. et al., (1992) Expression cloning of a human dual-specificity phosphatase. *Proc Natl Acad Sci USA* 89, 12170-4). VHR is a small enzyme with only 185 amino acids ($M_r$ 21 kDa), and it doesn't comprise any apparent targeting domain or docking site. The crystal structure of VHR has been solved, identifying a shallow active site that allows VHR to act on both phospho-tyrosine (pTyr) and phospho-threonine (pThr) (Yuvniyama, J. et al., (1996) Crystal structure of the dual specificity protein phosphatase VHR, *Science* 172, 1328-31). VHR has been reported to dephosphorylate the mitogen-activated protein kinases (MAP kinases) Erk and Jnk, but not p38 (Alonso, A. et al., (2001) Inhibitory role for dual specificity phosphatase VHR in T cell antigen receptor and CD28-induced Erk and Jnk activation. *J Biol Chem* 276, 4766-71; Todd, J. L. et al., (2002) Dual-specificity protein tyrosine phosphatase VHR down-regulates c-Jun N-terminal knase (NK), *Oncogene* 21, 2573-83, Todd, J. L. et al., (1999) Extracellular regulated kinases (ERK) 1 and ERK2 are authentic substrates for the dual-specificity protein-tyrosine phosphatase VHR. A novel role in down-regulating the ERK pathway. *J Bio Chem* 274, 13271-80). MAP kinases mediate major signaling pathways triggered by extracellular growth factor, stress, and cytokines (Waskiewicz, A. J. et al., (1995) Mitogen and stress response pathways: MAP kinase cascades and phosphatase regulation in mammals and yeast. *Curr Opin Cell Bio* 7, 798-805) and regulate cell differentiation, proliferation and apoptosis (Robinson, M. J. et al., (1997) Mitogen-activated protein kinase pathways. *Curr Opin Cell Biol* 9, 180-6; Ip, Y. T. et al., (1998) Signal transduction by the c-Jun N-terminal kinase (JNK)—from inflammation to development. *Curr Opin Cell Biol* 10, 205-19).

MAP-kinases are activated by phosphorylation at a Thr-X-Tyr motif in the activation loop (Canagarajah, B. J. et al., (1997) Activation mechanism of MAP kinase ERK2 by dual phosphorylation. *Cell* 90, 859-69) and then phosphorylate their cellular substrates, including many transcription factors required for the expression of cell cycle regulatory genes, such as cyclins that regulate cyclin-dependent kinases. The inactivation of MAP kinases is catalyzed by phosphatases that dephosphorylate the pThr and/or pTyr in the activation loop, such as VHR.

VHR is activated by phosphorylation at Y138 by the ZAP-70 tyrosine kinase (Alonso, A. et al., (2003) Tyrosine phosphorylation of VHR phosphatase by ZAP-70. *Nat. Immunol.* 4, 44-8) and probably other kinases. Unlike many other MAP kinase phosphatases (MKP's), VHR expression is not induced in response to activation of MAP kinases (Alonso, A. et al., (2001) Inhibitory role for dual specificity phosphatase VHR in T cell antigen receptor and CD28-induced Erk and Jnk activation. *J Biol Chem* 276, 4766-71), but is instead connected to cell cycle progression (Rahmouni, S. et al., (2006) Loss of VHR causes cell-cycle arrest and senescence. *Nat Cell Biol.* 8, 524-531). Using RNA interference to knock down endogenous VHR in HeLa carcinoma cells, cell cycle is arrested at G1 to S and G2 to M transitions and cells show signs of senescence, suggesting that VHR inhibition may be a useful approach to halt the growth of cancer cells. Loss of VHR decreases the expression of cell cycle regulators CDC2, CDK2 and CDK4, matching the results for cells entering senescence (Stein, G. H. et al., (1991) Senescent cells fail to express cdc2, cycA, and cycB in response to mitogen stimulation. *Proc Natl Acad Sci USA* 88, 11012-6), whereas the most up-regulated gene in VHR knock down is the CDK inhibitor $p21^{Cip\text{-}waf1}$. In synchronized cells, VHR is hardly detectable in G1 phase, and then slowly increases when cells go through cell cycle and peaked in M phase. When cells reach the next G1 phase, VHR levels are quickly back to minimal. When cells are treated with protein synthesis inhibitor cycloheximide, the half-life of VHR in G1 phase is much shortened, compared to other phases.

When VHR is knocked down there is a strong activation of Erk and Jnk, the only two substrates identified for VHR. Without VHR, activities of both Erk and Jnk are highly elevated after activation and there is a clear increase of the basal Erk activity (Rahmouni, ibid.). There have been several reports that prolonged activation of MAP kinase pathway results in cell cycle arrest and cell senescence (Woods, D. et al., (1997) Raf-induced proliferation or cell cycle arrest is determined by the level of Raf activity with arrest mediated by p21Cip1. *Mol Cell Biol* 17, 5598-611; Sewing, A. et al., (1997) High-intensity Raf signal causes cell cycle arrest mediated by p21Cip1. *Mol Cell Biol* 17, 5588-97; Serrano, M. et al., (1997) Oncogenic ras provokes premature cell senescence associated with accumulation of p53 and p16INK4a. *Cell* 88, 593-602; Pumiglia, K. M. et al., (1997) Cell cycle arrest mediated by the MEK/mitogen-activated protein kinase pathway. *Proc Natl Acad Sci USA* 94, 4448-52; Wang, W. et al. (2002) Sequential activation of the MEK-extracellular signal-regulated kinase and MKK3/6-p38 mitogen-activated protein kinase pathways mediates oncogenic ras-induced premature senescence. *Mol Cell Biol* 22, 3389-403). Elevated Erk is directly responsible for M-phase arrest, and inactivation of Erk is required to exit M-phase (Chau, A. S. et al., (1999) Inactivation of p42 mitogen-activated protein kinase is required for exit from M-phase after cyclin destruction. *J Biol Chem* 274, 32085-90). Also, Jnk activation has been linked to G1-phase arrest in response to growth inhibitory stimuli (Tchou, W. W. et al., (1999) Role of c-Jun N-terminal kinase 1 (JNK-1) in cell cycle checkpoint activated by the protease inhibitor N-acetyl-leucinyl-leucinyl-norleucinal. *Oncogene* 18, 6974-80; Grosch, S. et al., (2003) Activation of c-Jun-N-terminal-kinase is crucial for the induction of a cell cycle arrest in human colon carcinoma cells caused by flurbiprofen enantiomers. *Faseb J* 17, 1316-8). Stress has been shown to activate Jnk and to induce p53 and $21^{Cip-waf1}$ expression (Xue, Y. et al., (2003) Association of JNK1 with p21waf1 and p53: modulation of JNK1 activity. *Mol Carcinog* 36, 38-44). Jnk has been confirmed to be physically interacting with p53 and $21^{Cip-waf1}$ (Xue ibid.). Loss of VHR induced cell cycle arrest is dependent on the hyperactivation of Erk and Jnk, with Erk responsible for G2-M arrest and Jnk responsible of the G1-S arrest (Rahmouni ibid.).

The first VHR small molecule inhibitor to be described was the tetronic acid derivative RK-682 which was isolated from a *Streptomyces* strain as a PTP inhibitor in a microbial metabolites screening (Hamaguchi, T. et al., (1995) Rk-682, a potent inhibitor of tyrosine phosphatase, arrested the mammalian cell cycle progression at G1 phase. *FEBS Lett.* 372, 54-58). In vitro, RK-682 inhibited cell cycle progression of Ball-1 cells, arresting them at the G1/S cell cycle phase transition. However, RK-682 was found to have several other inhibitory activities, including phospholipase A2 inhibition (Shinagawa, S. et al., (1993) Tetronic acid derivatives, its manufacturing methods and uses. Japan. Kokai Tokyo Koho, JP 05-43568, 1-26), HIV-1 protease inhibition (Roggo, B. E. et al., (1994) 3-alkanoyl-5-hydroxymethyl tetronic acid homologues and resistomycin: new inhibitors of HIV-1 protease. I. Fermentation, isolation and biological activity. *J Antibiot.* (Tokyo) 47, 136-42; Roggo, B. E. et al., (1994) 3-alkanoyl-5-hydroxymethyl tetronic acid homologues: new inhibitors of HIV-1 protease. II. Structure determination. *J. Antibiot.* (Tokyo) 47, 143-7.) and heparanase inhibition (Ishida, K. et al., (2004) Exploitation of heparanase inhibitors from microbial metabolites using an efficient visual screening system. *J Antibiot.* 57, 136-42).

SUMMARY

The present disclosure relates to compounds that inhibit *Vaccinia* H1-related (VHR) protein tyrosine phosphatase (PTP) and thereby provides a method for treating cancer. The present disclosure also relates to compounds that are VHR protein tyrosine phosphatase inhibitors and to compositions comprising the same.

BRIEF DESCRIPTION OF THE FIGURES

FIG. 1 depicts the Lineweaver-Burk plot showing competitive inhibition of VHR by 2-[(Z)-4-oxo-5-((E)-3-phenylallylidene)-2-thioxothiazolidin-3-yl]ethane-sulfonic acid.

DETAILED DESCRIPTION

In this specification and in the claims that follow, reference will be made to a number of terms, which shall be defined to have the following meanings:

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

An organic radical can have, for example, 1-26 carbon atoms, 1-18 carbon atoms, 1-12 carbon atoms, 1-8 carbon atoms, or 1-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Substituted and unsubstituted linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 2,2,2-trifluoroethyl ($C_3$), 3-carboxypropyl ($C_3$), 2,3-dihydroxycyclobutyl ($C_4$), and the like.

Substituted and unsubstituted linear, branched, or cyclic alkenyl include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

Substituted and unsubstituted linear or branched alkynyl include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

The term "aryl" as used herein denotes organic rings that consist only of a conjugated planar carbon ring system with delocalized pi electrons, non-limiting examples of which include phenyl ($C_6$), naphthylen-1-yl ($C_{10}$), naphthylen-2-yl ($C_{10}$). Aryl rings can have one or more hydrogen atoms substituted by another organic or inorganic radical. Non-limiting examples of substituted aryl rings include: 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$).

The term "heteroaryl" denotes an aromatic ring system having from 5 to 10 atoms. The rings can be a single ring, for example, a ring having 5 or 6 atoms wherein at least one ring atom is a heteroatom not limited to nitrogen, oxygen, or sulfur. Or "heteroaryl" can denote a fused ring system having 8 to 10 atoms wherein at least one of the rings is an aromatic ring and at least one atom of the aromatic ring is a heteroatom not limited nitrogen, oxygen, or sulfur.

The following are non-limiting examples of heteroaryl rings according to the present disclosure:

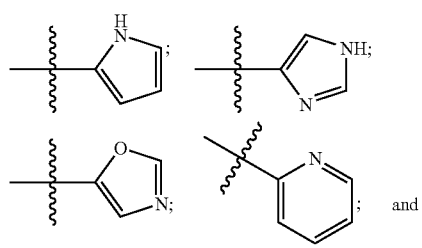

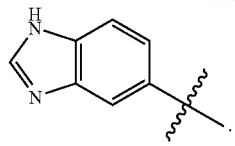

The term "heterocyclic" denotes a ring system having from 3 to 10 atoms wherein at least one of the ring atoms is a heteroatom not limited to nitrogen, oxygen, or sulfur. The rings can be single rings, fused rings, or bicyclic rings. Non-limiting examples of heterocyclic rings include:

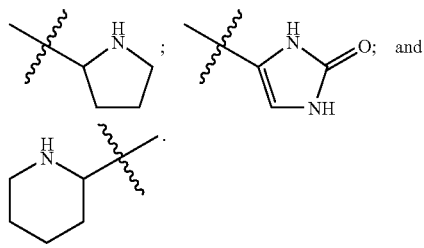

All of the aforementioned heteroaryl or heterocyclic rings can be optionally substituted with one or more substitutes for hydrogen as described herein further.

Throughout the description of the present disclosure the terms having the spelling "thiophene-2-yl and thiophene-3-yl" are used to describe the heteroaryl units having the respective formulae:

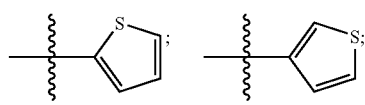

whereas in naming the compounds of the present disclosure, the chemical nomenclature for these moieties are typically spelled "thiophen-2-yl and thiophen-3-yl" respectively. Herein the terms "thiophene-2-yl and thiophene-3-yl" are used when describing these rings as units or moieties which make up the compounds of the present disclosure solely to make it unambiguous to the artisan of ordinary skill which rings are referred to herein.

The term "substituted" is used throughout the specification. The term "substituted" is defined herein as a unit, whether acyclic or cyclic, that has one or more hydrogen atoms replaced by one or more units as defined further herein. The following are non-limiting examples of units that can substitute for hydrogen atoms:

i) $C_1$-$C_{12}$ linear, branched, or cyclic alkyl, alkenyl, and alkynyl; for example, methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_1$-$C_9$ heterocyclic rings; as described herein below;
iv) substituted or unsubstituted $C_1$-$C_9$ heteroaryl rings; as described herein below;
v) —$(CR^{14a}R^{14b})_zOR^{13}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vi) —$(CR^{14a}R^{14b})_zC(O)R^{13}$; for example, —$COCH_3$, —$CH_2COCH_3$, —$OCH_2CH_3$, —$CH_2COCH_2CH_3$, —$COCH_2CH_2CH_3$, and —$CH_2COCH_2CH_2CH_3$;
vii) —$(CR^{14a}R^{14b})_zC(O)OR^{13}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
viii) —$(CR^{14a}R^{14b})_zC(O)N(R^{13})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
ix) —$(CR^{14a}R^{14b})_zN(R^{13})_2$; for example, —$NH_2$, —$CH_2NH_2$, —$NHCH_3$, —$N(CH_3)_2$, —$NH(CH_2CH_3)$, —$CH_2NHCH_3$, —$CH_2N(CH_3)_2$, and —$CH_2NH(CH_2CH_3)$;
x) halogen; —F, —Cl, —Br, and —I;
xi) —$(CR^{14a}R^{14b})_zCN$;
xii) —$(CR^{14a}R^{14b})_zNO_2$;
xiii) —$CH_jX_k$; wherein X is halogen, j is from 0 to 2, j+k=3; for example, —$CH_2F$, —$CHF_2$, —$CF_3$, —$CCl_3$, or —$CBr_3$;
xiv) —$(CR^{14a}R^{14b})_zSR^{13}$; —SH, —$CH_2SH$, —$SCH_3$, —$CH_2SCH_3$, —$SC_6H_5$, and —$CH_2SC_6H_5$;
xv) —$(CR^{14a}R^{14b})_zSO_2R^{13}$; —$SO_2H$, —$CH_2SO_2H$, —$SO_2CH_3$, —$CH_2SO_2CH_3$, —$SO_2C_6H_5$, and —$CH_2SO_2C_6H_5$; and
xiii) —$(CR^{14a}R^{14b})_zSO_3R^{13}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{13}$ is independently hydrogen, substituted or unsubstituted $C_1$-$C_4$ linear, branched, or cyclic alkyl, phenyl, benzyl; or two $R^{13}$ units can be taken together to form a ring comprising 3-7 atoms; $R^{14a}$ and $R^{14b}$ are each independently hydrogen or $C_1$-$C_4$ linear or branched alkyl; the index p is from 0 to 4.

For the purposes of the present disclosure the terms "compound," "analog," and "composition of matter" stand equally well for the chemical entities described herein, including all enantiomeric forms, diastereomeric forms, salts, and the like, and the terms "compound," "analog," and "composition of matter" are used interchangeably throughout the present specification.

The first aspect of compounds of the present disclosure have Formula (I):

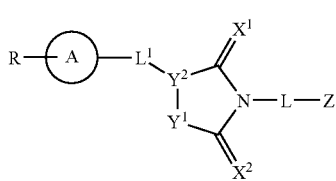

(I)

and the second aspect of compounds of the present disclosure have Formula (II):

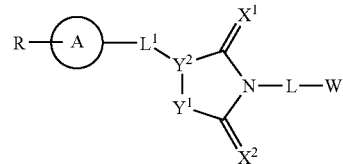

wherein the units A, L, $L^1$, R, $X^1$, $X^2$, $Y^1$, $Y^2$, W, and Z are further described herein below.

The compounds of the present disclosure comprise a 5- or 6-member "core ring" wherein $X^1$, $X^2$, $Y^1$, and $Y^2$ can comprise various elements as described herein below. To this core ring is attached an A unit that is a ring having from 5 to 10 ring atoms. The A unit can be further optionally substituted by one or more R units as defined herein. The A unit is linked to the core ring by linking unit $L^1$. $L^1$ can be a single bond or a double bond between the A unit and the core unit, or $L^1$ can comprise from 1 to 3 atoms. Z units are further defined herein and are linked to the core ring nitrogen atom by a linking unit L wherein L contains from 1 to 3 carbon atoms.

Core Rings

The core rings of the present disclosure can be any 5-member or 6-member ring within the definition of $X^1$, $X^2$, $Y^1$, and $Y^2$. $Y^1$ and $Y^2$ are each independently units containing one or two carbon atoms or a unit containing a carbon and a nitrogen atom, wherein any of the carbon or nitrogen atoms can be further substituted by one or more organic radicals having from 1 to 6 carbon atoms and/or heteroatoms, including, nitrogen, oxygen, and sulfur, and can be further substituted by one or more organic radicals including alkyl, alkoxy, amino, halogen, cyano, thio, thioalkyl, and the like.

In one example of compounds having Formula (I), $Y^1$ can comprise any of the following units chosen from:
i) —$C(R^{2a})(R^{2b})$—;
ii) —$N(R^3)$—;
iii) —$C(R^{2a})(R^{2b})C(R^{2c})(R^{2d})$—;
iv) —$C(R^{2a})(R^{2b})N(R^3)$—;
v) —$C(R^{2a})$=N—;
vi) —O—; or
vii) —S—;

wherein $R^{2a}$, $R^{2b}$, $R^{2c}$, and $R^{2d}$ are each organic radicals independently chosen from:
i) —H;
ii) $C_1$-$C_4$ substituted or unsubstituted alkyl;
iii) $C_1$-$C_4$ substituted or unsubstituted alkoxy;
iv) —OH;
v) halogen, for example, —F, —Cl, —Br, and —I; or
vi) —CN.

Also $R^{2a}$ and $R^{2b}$ or $R^{2c}$ and $R^{2d}$ can be taken together to form a unit having the formula =$X^3$, wherein $X^3$ is O, S, or NH; for example, units having the formula: =O, =S, and =NH. $R^3$ is hydrogen or $C_1$-$C_4$ alkyl.

Compounds of Formula (I) can comprise $Y^2$ units having from 1 to 3 carbon atoms or 1 or 2 carbon atoms in combination with a heteroatom, including nitrogen, sulfur, and oxygen. In one example of compound having Formula (I), $Y^2$ is —$C(R^4)$—, —N—, or $Y^2$ can form an exocyclic double bond to either $L^1$ or directly to the A unit; wherein $R^4$ is hydrogen, methyl, or ethyl. In addition, A rings can comprise $Y^1$ and $Y^2$ that are taken together to form units having the formulae:

—$C(R^{2a})$=C— or —N=C—;

wherein $R^{2a}$ is the same as defined herein above.

$X^1$ and $X^2$ are each independently chosen from O, S, or NH; for example, $X^1$ and $X^2$ are each independently units having the formulae: =O, =S, and =NH.

One example of 5-member core rings according to Formula (I) has the formula:

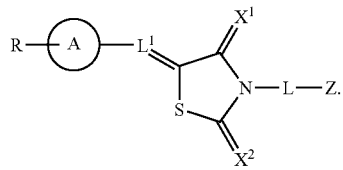

Included in this example of compounds according to Formula (I) are 5-member core rings having the formula:

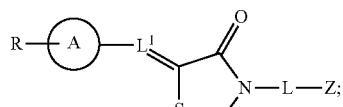

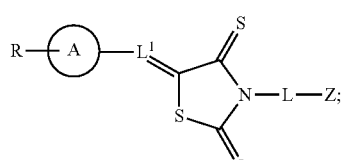

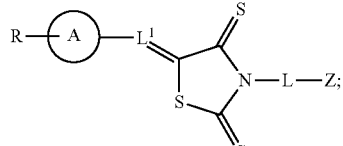

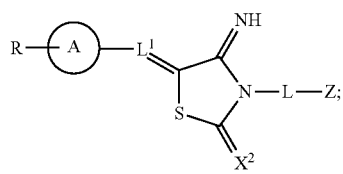

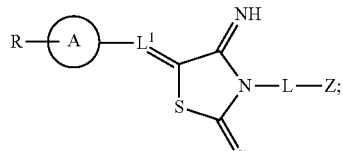

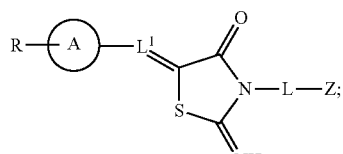

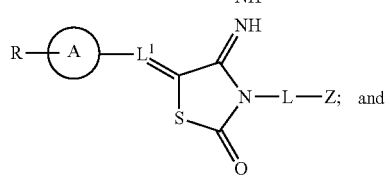

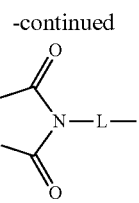

Another example of 5-member core rings according to Formula (I) has the formula:

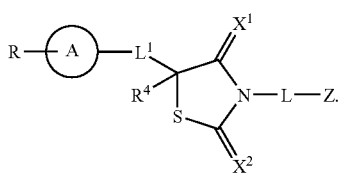

Included in this example are 5-member core rings having the formula:

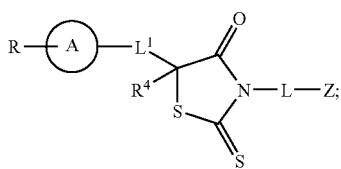

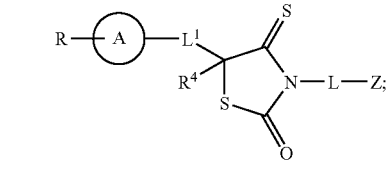

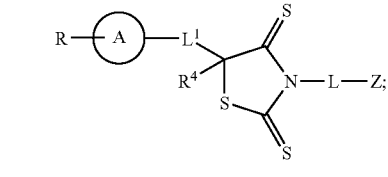

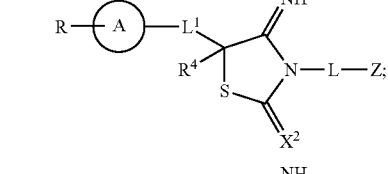

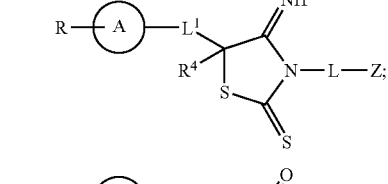

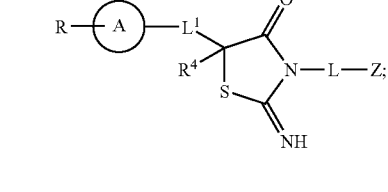

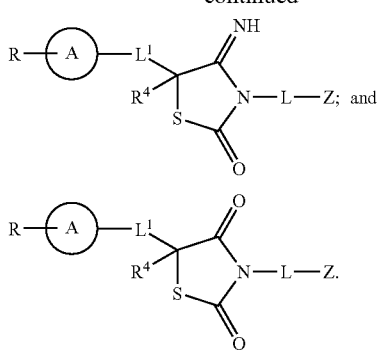

A further example of 5-member core rings according to Formula (I) has the formula:

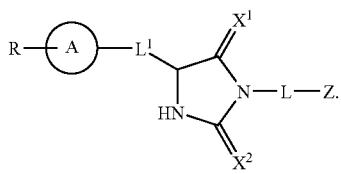

Included in this example are 5-member core rings having the formula:

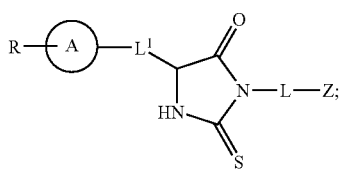

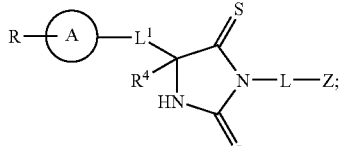

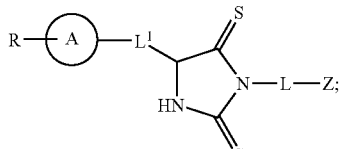

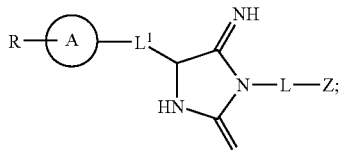

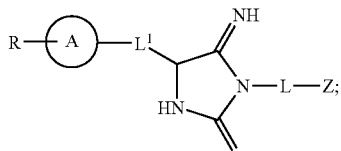

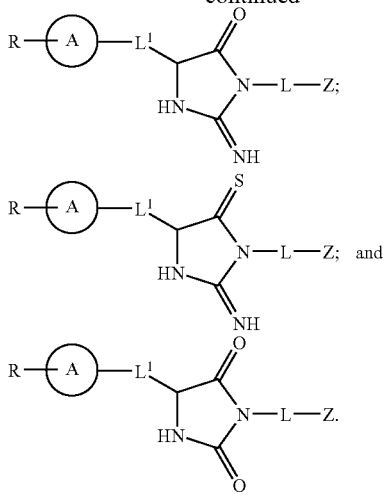

A yet further example of 5-member core rings according to Formula (I) has the formula:

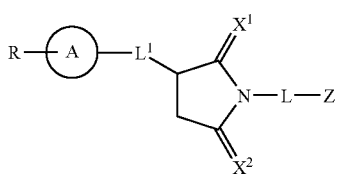

Examples of 6-member core rings according to Formula (I) have the formula:

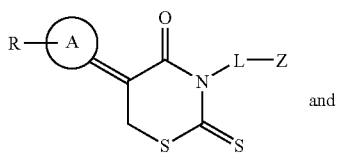

and

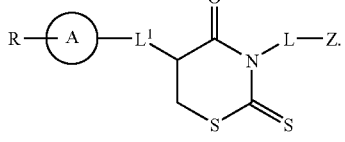

In one example of compounds having Formula (II), $Y^1$ can comprise any of the following units chosen from:
  i) $-C(R^{2a})(R^{2b})-$;
  ii) $-N(R^3)-$;
  iii) $-C(R^{2a})(R^{2b})C(R^{2c})(R^{2d})-$;
  iv) $-C(R^{2a})(R^{2b})N(R^3)-$;
  v) $-C(R^{2a})=N-$;
  vi) $-O-$; or
  vii) $-S-$;
wherein $R^{2a}$, $R^{2b}$, $R^{2c}$, and $R^{2d}$ are each organic radicals independently chosen from:
  i) $-H$;
  ii) $C_1$-$C_4$ substituted or unsubstituted alkyl;
  iii) $C_1$-$C_4$ substituted or unsubstituted alkoxy;
  iv) $-OH$;
  v) halogen, for example, $-F$, $-Cl$, $-Br$, and $-I$; or
  vi) $-CN$.

Also $R^{2a}$ and $R^{2b}$ or $R^{2c}$ and $R^{2d}$ can be taken together to form a unit having the formula $=X^3$, wherein $X^3$ is O, S, or NH; for example, units having the formula: $=O$, $=S$, and $=NH$. $R^3$ is hydrogen or $C_1$-$C_4$ alkyl.

Compounds of Formula (II) can comprise $Y^2$ units having from 1 to 3 carbon atoms or 1 or 2 carbon atoms in combination with a heteroatom, including nitrogen, sulfur, and oxygen. In one example of compound having Formula (I), $Y^2$ is $-C(R^4)-$, $-N-$, or $Y^2$ can form an exocyclic double bond to either $L^1$ or directly to the A unit; wherein $R^4$ is hydrogen, methyl, or ethyl. In addition, A rings can comprise $Y^1$ and $Y^2$ that are taken together to form units having the formulae:

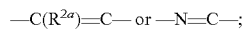

wherein $R^{2a}$ is the same as defined herein above.

$X^1$ and $X^2$ are each independently chosen from O, S, or NH; for example, $X^1$ and $X^2$ are each independently units having the formulae: $=O$, $=S$, and $=NH$.

One example of 5-member core rings according to Formula (II) has the formula:

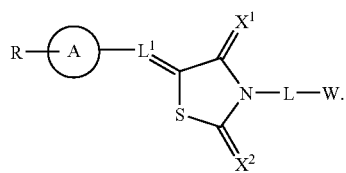

Included in this example of compounds according to Formula (II) are 5-member core rings having the formula:

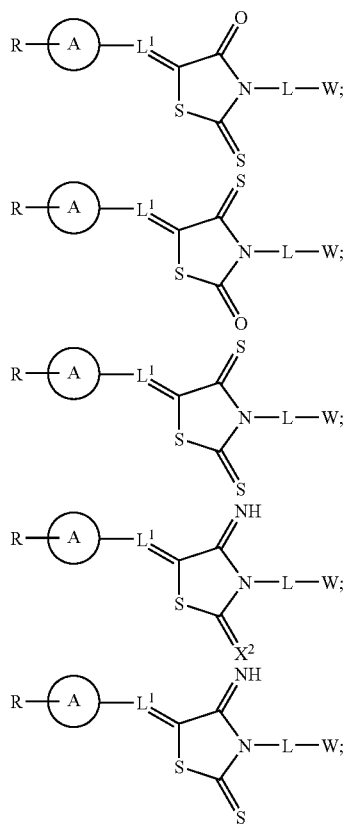

Another example of 5-member core rings according to Formula (II) has the formula:

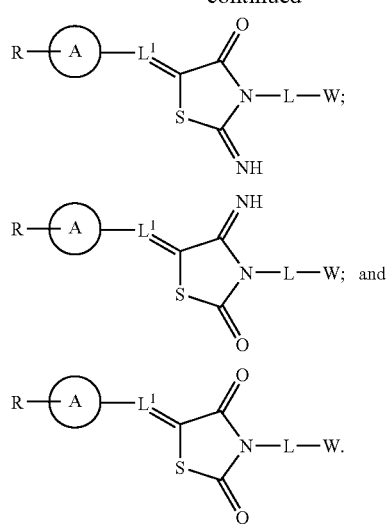

Included in this example are 5-member core rings having the formula:

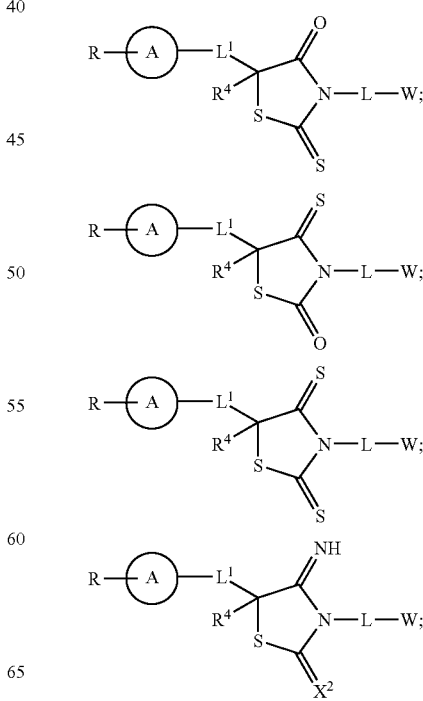

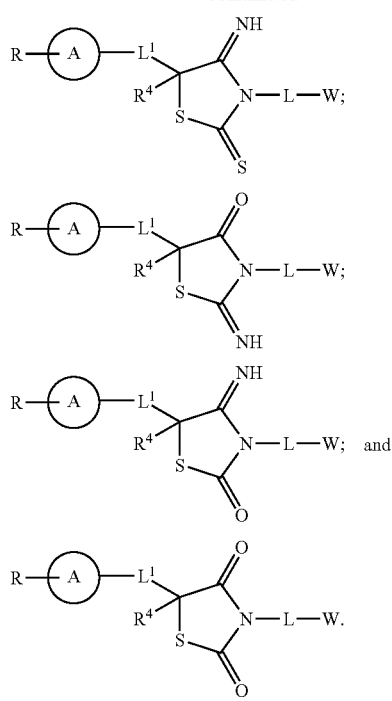

A further example of 5-member core rings according to Formula (II) has the formula:

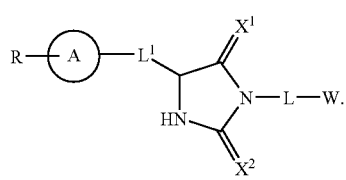

Included in this example are 5-member core rings having the formula:

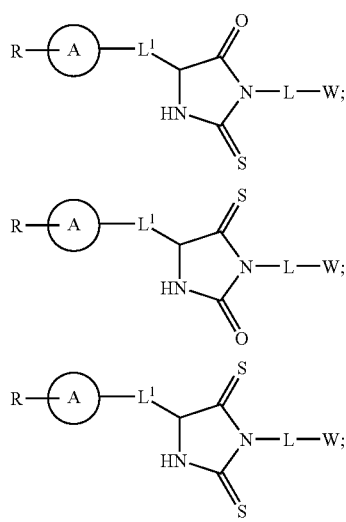

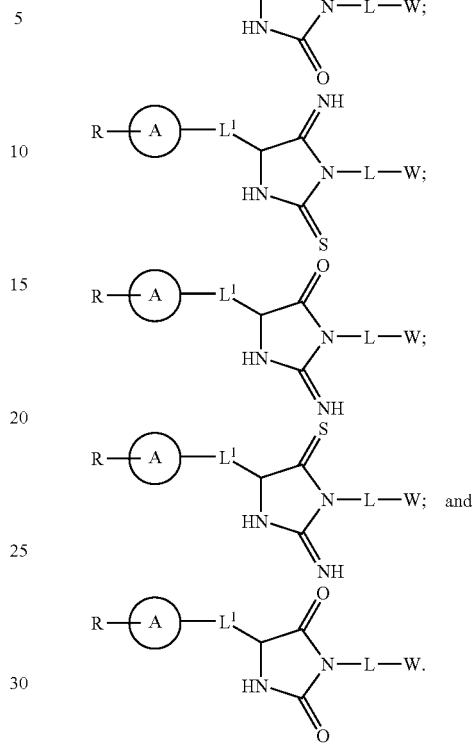

A yet further example of 5-member core rings according to Formula (II) has the formula:

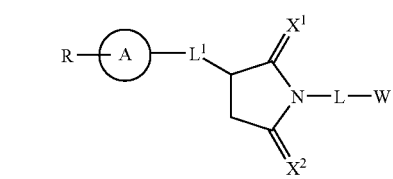

Examples of 6-member core rings according to Formula (II) have the formula:

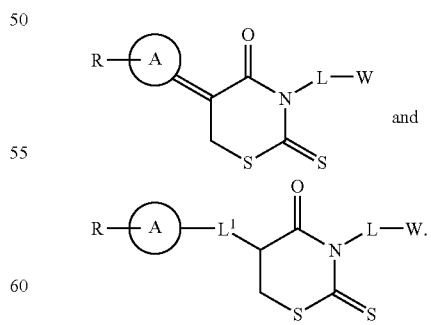

Z Units

Z is a carboxy, keto, sulfonic acid, sulfonamide, alkylsulphonamide, phosphonic acid, or phosphonic ester radical. One example of Z units according to Formula (I) includes sulfonic acids and salts thereof. When taken together with the core ring system this example has the formula:

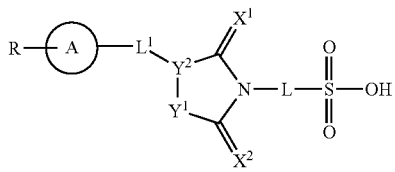

for the free acid and the formula:

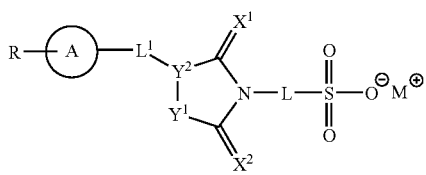

for the pharmaceutically acceptable salt form. $M^+$ represents a pharmaceutically acceptable cation or mixture of cations that provide electronic neutrality. Included herein are salts wherein the valence of the cation is greater than 1, for example, salts having the formula:

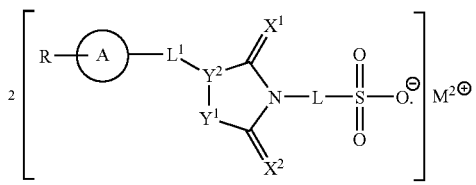

Non-limiting examples of cations include lithium, sodium, potassium, magnesium, calcium, barium, ammonium, and quaternary ammonium.

Another example of Z units according to Formula (I) includes compounds wherein Z is a carboxylic acid or pharmaceutically acceptable salt thereof. When taken together the core ring system this example has the formula:

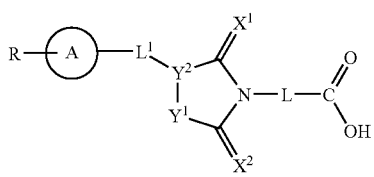

for the free acid and the formula:

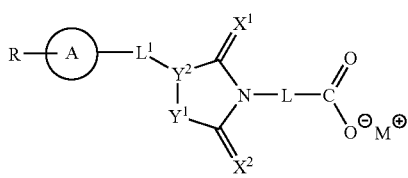

for the pharmaceutically acceptable salt form. As with sulphonic acids $M^+$ represents a pharmaceutically acceptable cation capable of providing electronic neutrality to the molecule.

The carboxylic acids can also be bis carboxylic acids, for example, units when taken with the ring system, have the formula:

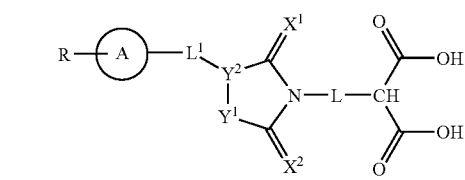

for the free acid and the formula:

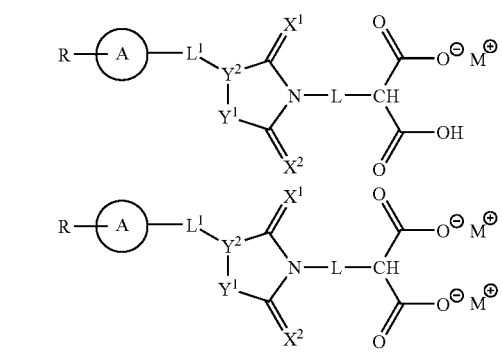

for the pharmaceutically acceptable salt forms. As with the carboxylic acids $M^+$ represents a pharmaceutically acceptable cation capable of providing electronic neutrality to the molecule. For example, only one $M^{2+}$ can be present in the dicarboxylic acid salt above.

Z units can further comprise malonic acid esters, for example, compounds having the formula:

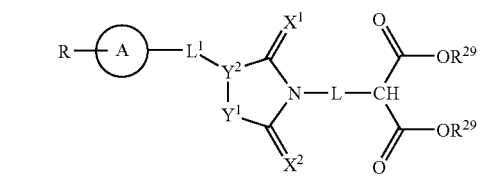

wherein $R^{29}$ is chosen from hydrogen or $C_1$-$C_4$ linear or branched alkyl. For example, one $R^{29}$ can be hydrogen and the other $R^{29}$ can be methyl thus forming the mixed malonic acid ester. In addition, salts of this mixed acid ester having the formula:

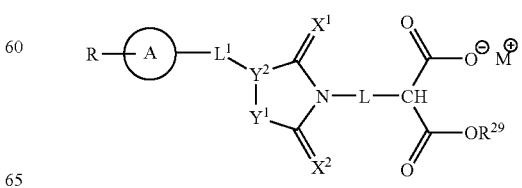

are also included herein.

Further examples of Z units according to Formula (I) include ketoesters having the formula —C(O)C(O)OR$^{28}$, for example, —C(O)C(O)OCH$_3$, and oxalimides having the formula —NHC(O)C(O)OR$^{28}$, for example, —NHC(O)C(O)OCH$_3$ wherein R$^{28}$ is hydrogen or C$_1$-C$_4$ alkyl.

A further example of Z units according to Formula (I) includes compounds wherein Z is a keto unit having the formula —C(O)R$^1$ wherein R$^1$ is C$_1$-C$_4$ linear or branched alkyl. Non-limiting example of Z units include —C(O)CH$_3$, —C(O)CH$_2$CH$_3$, and —C(O)CH(CH$_3$)$_2$.

A yet further example of Z units according to Formula (I) includes compounds wherein Z is a sulfonamide unit having the formula —S(O)$_2$NH$_2$.

A still further example of Z units according to Formula (I) includes compounds wherein Z is an alkyl or substituted alkyl sulfonamide, for example, —NHS(O)$_2$CH$_3$, —NHS(O)$_2$CH$_2$CH$_3$, —NHS(O)$_2$CF$_3$, A yet still further example of Z units according to Formula (I) includes compounds wherein Z is a phosphonic acid or ester, for example, compounds having the formula:

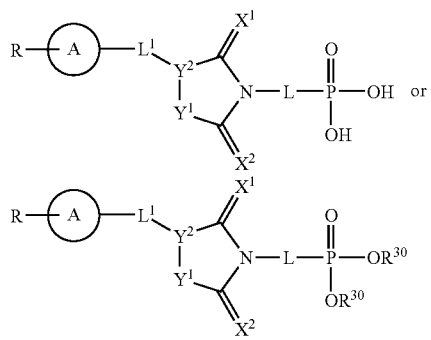

wherein each R$^{30}$ is independently C$_1$-C$_4$ linear alkyl.

W Units

W units encompass radicals that comprise one or more rings. A first embodiment of W units includes derivatives of barbituric acid that when taken with the core ring and L units have the formula:

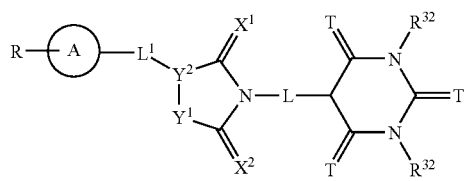

wherein T is O, S, or NH, and each R$^{32}$ is independently hydrogen or C$_1$-C$_4$ alkyl. Non-limiting examples of this embodiment includes:

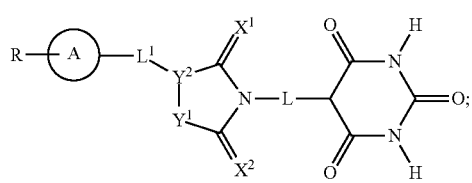

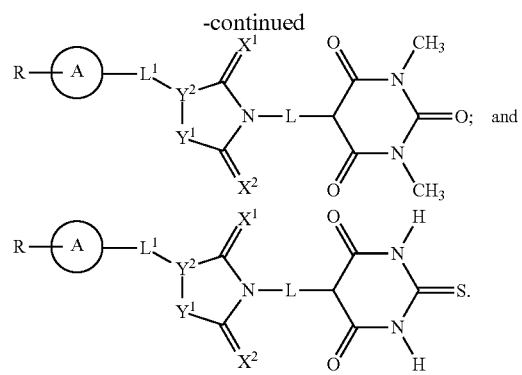

Another embodiment of W units includes organic radicals that are lactones or lactams, for example,

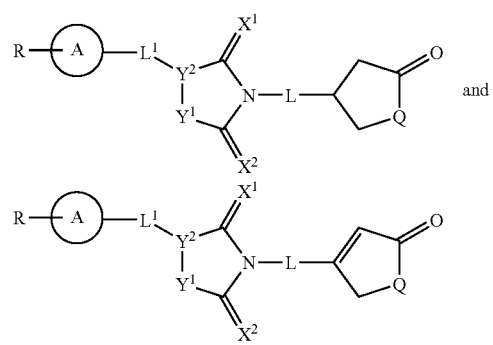

wherein Q is O or NH.

A yet further embodiment includes 5-member heterocyclic and heteroaryl rings as defined herein above. Non-limiting examples include tetrazol-5-yl, 1,2,3-triazol-4-yl, 1,2,4-triazol-3-yl, and 1,2,4-triazol-5-yl.

Further embodiments of W units include thio-vanadyl esters, phenylarsine oxides, and dephostatin and derivatives thereof.

L Units

L is a linking group containing 1 to 3 carbon atoms. One example of L units according to Formula (I) are units chosen from methylene (—CH$_2$—), ethylene (—CH$_2$CH$_2$—), and propylene (—CH$_2$CH$_2$CH$_2$—).

A further example of L units according to Formula (I) are substituted alkylene units, for example, (—CF$_2$—), (—CH$_2$CF$_2$—), (—CF$_2$CH$_2$—), and (—CFHCFH—). When combined with the core ring, this example of L units provides compounds having the formula, for example:

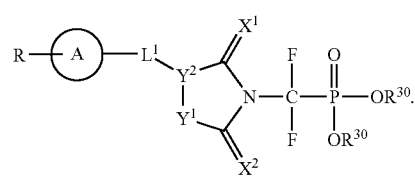

L$^1$ Units

L$^1$ units connect the core ring with the A ring and can comprise from 1 to 5 carbon atoms that can be further substituted by alkyl radicals having 1 or 2 carbon atoms. One example of L$^1$ linking units according to Formula (I) includes a direct chemical bonds, for example, a single covalent bond, a double bond, or a unit containing from 1 to 3 atoms. The double bond can be exocyclic to the core ring, exocyclic to the A ring, or be otherwise contained in the $L^1$ unit. Examples of $L^1$ according to Formula (I) include the following:

i) a single or a double bond:

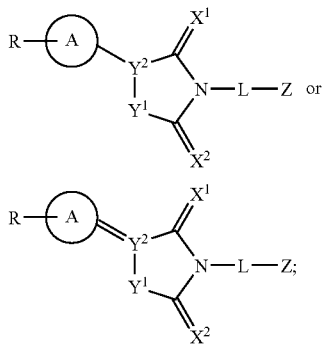

ii) a one carbon atom unit:

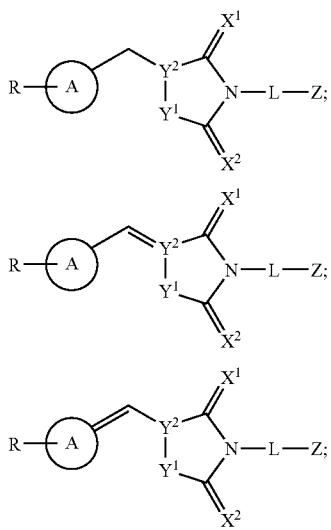

iii) a two carbon atom unit:

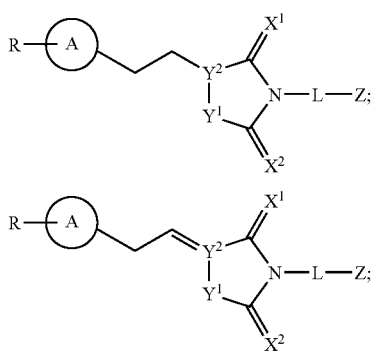

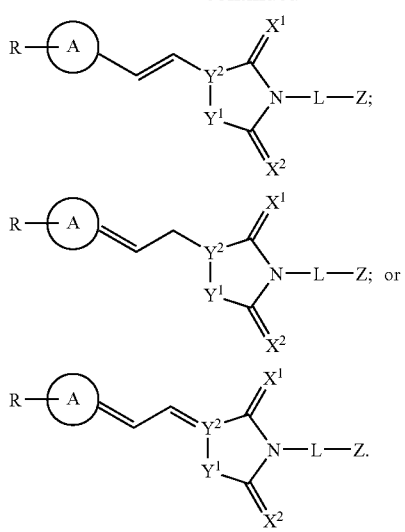

A Units

The A units according to Formula (I) can be any ring comprising from 3 to 20 ring atoms including heteroatoms, for example, nitrogen, sulfur, and oxygen, or mixtures of two or more heteroatoms. The A units according to Formula (I) can be mono-cyclic, bi-cyclic, fused rings, or spirocyclic. The A units can have one or more or the ring atom hydrogen atoms substituted by an organic or inorganic radical, not limited to, alkyl, alkoxy, hydroxy, carboxy, cyano, thio, thioalkyl, phenyl, benzyl, or two hydrogen atoms on the same ring carbon atom can be taken together to form a carbonyl unit or an imide.

One example of compounds according to Formula (I) include phenyl or a heteroaryl or heterocyclic ring having from 5 to 10 ring atoms wherein the ring atoms can be further substituted by one or more R units. Non-limiting examples of 5-member and 6-member ring heteroaryl units include pyrrolyl, pyrazolyl, imidazolyl, [1,2,3]triazolyl, [1,2,4]triazolyl, tetrazolyl, [1,3,4]oxadiazolyl, [1,2,4]oxadiazolyl, oxazolyl, isoxazolyl, furanyl, thiophenyl, pyridinyl, pyrimidinyl, pyrazinyl, and triazinyl.

One example of A units includes 5-member heteroaryl rings chosen from

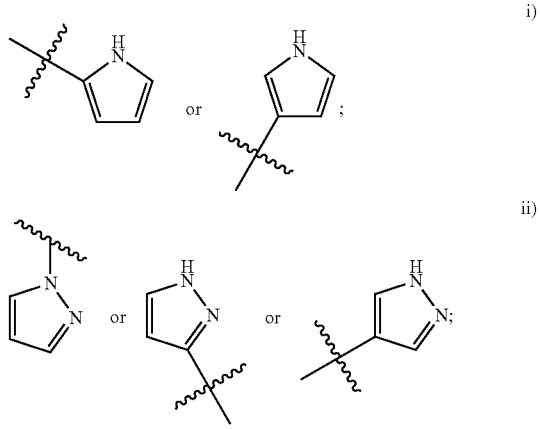

-continued iii) 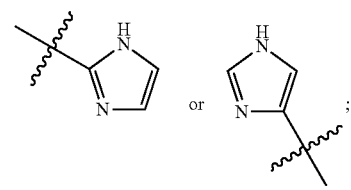

iv) 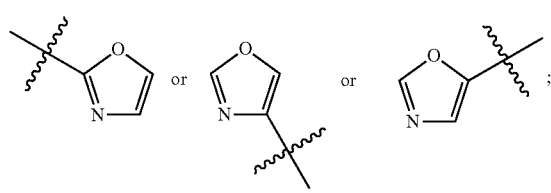

v) 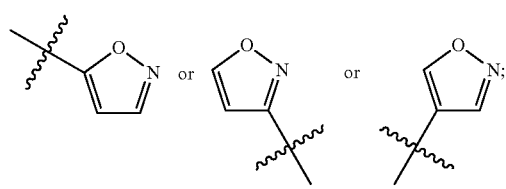

vi) 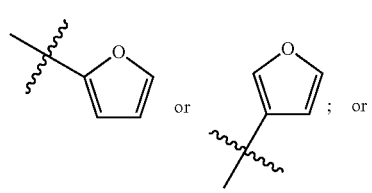

vii) 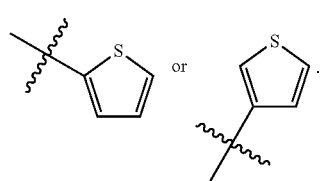

The 5-member ring heteroaryl units can have from 1 to 3 hydrogen atoms of the ring that are substituted by an R unit depending upon the choice of heteroaryl units, for example, the 1H-pyrazol-4-yl A ring having the formula:

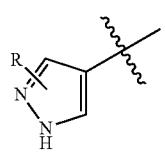

can be substituted with from 1 to 3 R units, an example of which includes:

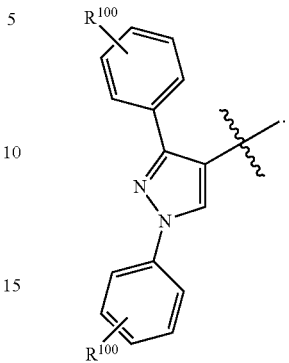

A further example is a substituted pyrrolyl A ring having the formula:

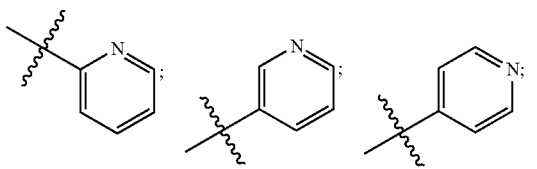

wherein $R^{100}$ represents from 1 to 5 organic radicals that can substitute for hydrogen atoms.

Another example of A units includes 6-member heteroaryl units chosen from:

i) 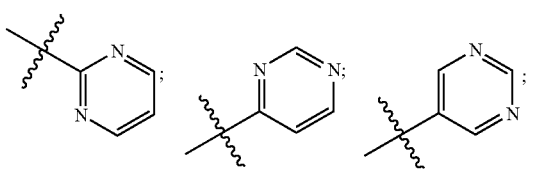

ii)

iii) 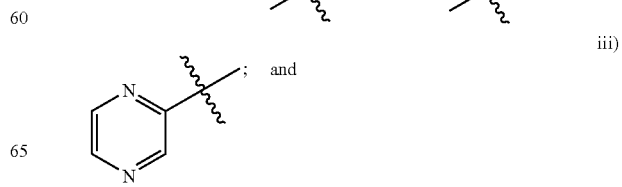; and iv)
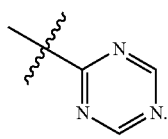
A further example of A rings includes 9-member and 10-member heterocyclic units having the formula:
i)
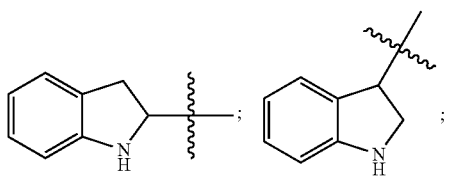
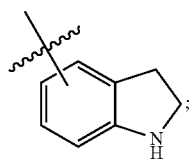
ii)
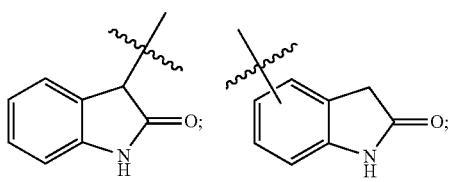
iii)
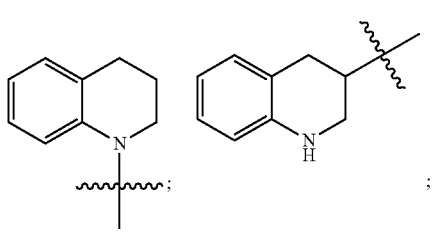
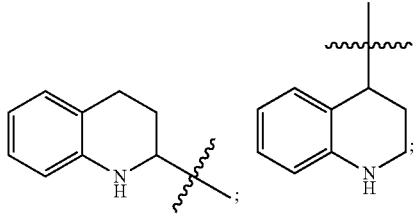
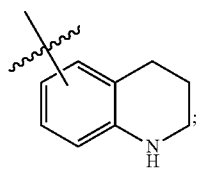
iv)
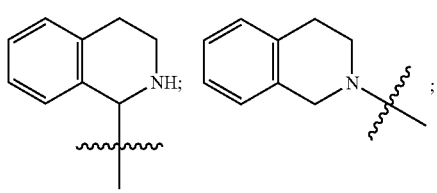
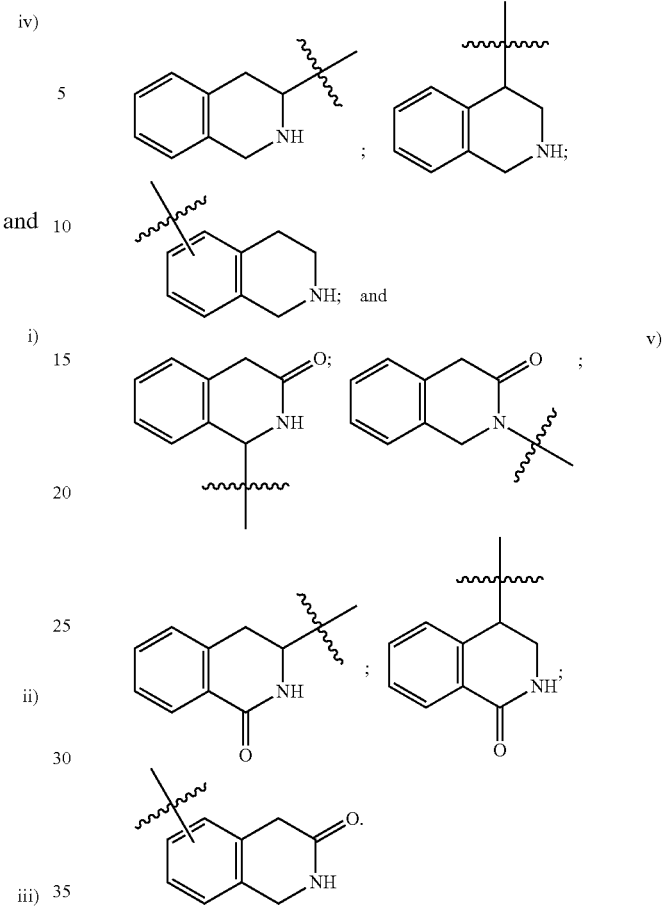
v)
On example of a herein disclosed compound having a 9-member heterocyclic rings includes:
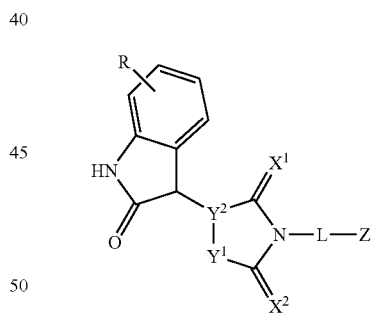
wherein R represents from 1 to 5 optional substitutions for hydrogen, examples of which include:
iv)
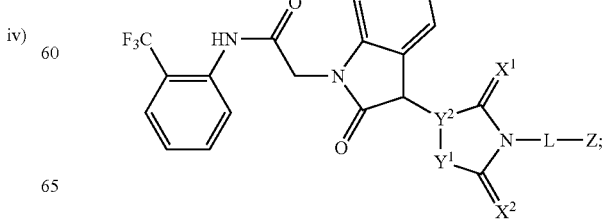

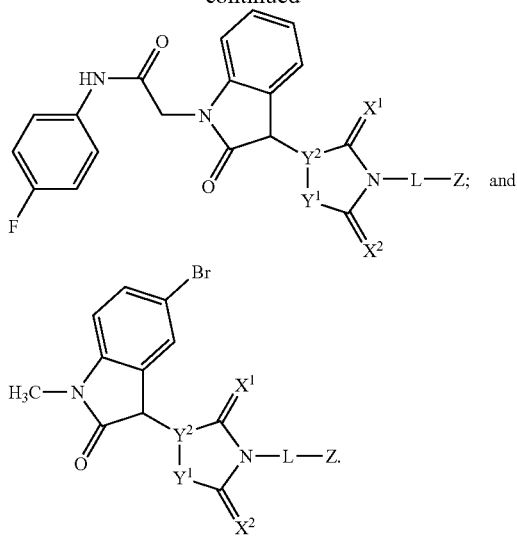

A units can also comprise phenyl rings substituted by one or more R units.

The A units of the present disclosure can have one or more hydrogen atoms substituted by one or more R units. One example of R units includes units that are independently chosen from:
i) alkyl, alkenyl, or alkynyl;
ii) aryl;
iii) heterocyclic; or
iv) heteroaryl;
that can be further substituted by one or more organic radicals.

A further example of R units includes units that are independently chosen from:
i) $C_1$-$C_{12}$ substituted or unsubstituted linear, branched, or cyclic alkyl;
ii) $C_2$-$C_{12}$ substituted or unsubstituted linear, branched, or cyclic alkenyl;
iii) $C_2$-$C_{12}$ substituted or unsubstituted linear or branched alkynyl;
iv) $C_6$ or $C_{10}$ substituted or unsubstituted aryl;
v) $C_1$-$C_9$ substituted or unsubstituted heterocyclic;
vi) $C_1$-$C_{11}$ substituted or unsubstituted heteroaryl;
vii) —[C($R^{21a}$)($R^{21b}$)]$_x$O$R^7$;
  $R^7$ is chosen from:
  a) —H;
  b) $C_1$-$C_{12}$ substituted or unsubstituted linear, branched, or cyclic alkyl;
  c) $C_6$ or $C_{10}$ substituted or unsubstituted aryl or alkylenearyl;
  d) $C_1$-$C_9$ substituted or unsubstituted heterocyclic;
  e) $C_1$-$C_{11}$ substituted or unsubstituted heteroaryl;
viii) —[C($R^{21a}$)($R^{21b}$)]$_x$N($R^{8a}$)($R^{8b}$);
  $R^{8a}$ and $R^{8b}$ are each independently chosen from:
  a) —H;
  b) —O$R^9$;
    $R^9$ is hydrogen or $C_1$-$C_4$ linear alkyl;
  c) $C_1$-$C_{12}$ substituted or unsubstituted linear, branched, or cyclic alkyl;
  d) $C_6$ or $C_{10}$ substituted or unsubstituted aryl;
  e) $C_1$-$C_9$ substituted or unsubstituted heterocyclic;
  f) $C_1$-$C_{11}$ substituted or unsubstituted heteroaryl; or
  g) $R^{8a}$ and $R^{8b}$ can be taken together to form a substituted or unsubstituted ring having from 3 to 10 carbon atoms and from 0 to 3 heteroatoms chosen from oxygen, nitrogen, and sulfur;
ix) —[C($R^{21a}$)($R^{21b}$)]$_x$C(O)$R^{11}$;
  $R^{11}$ is
  a) $C_1$-$C_{12}$ substituted or unsubstituted linear, branched, or cyclic alkyl;
  b) —O$R^{12}$;
    $R^{12}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
  c) —N($R^{13a}$)($R^{13b}$);
    $R^{13a}$ and $R^{13b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{3a}$ and $R^{3b}$ can be taken together to form a substituted or unsubstituted ring having from 3 to 10 carbon atoms and from 0 to 3 heteroatoms chosen from oxygen, nitrogen, and sulfur;
x) —[C($R^{21a}$)($R^{21b}$)]$_x$OC(O)$R^{14}$;
  $R^{14}$ is
  a) $C_1$-$C_{12}$ substituted or unsubstituted linear, branched, or cyclic alkyl;
  b) —N($R^{15a}$)($R^{15b}$);
    $R^{15a}$ and $R^{15b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;
xi) —[C($R^{21a}$)($R^{21b}$)]$_x$N$R^{16}$C(O)$R^{17}$;
  $R^{16}$ is:
  a) —H; or
  b) $C_1$-$C_4$ substituted or unsubstituted linear, branched, or cyclic alkyl;
  $R^{17}$ is
  a) $C_1$-$C_{12}$ substituted or unsubstituted linear, branched, or cyclic alkyl;
  b) —N($R^{18a}$)($R^{18b}$);
    $R^{18a}$ and $R^{18b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{18a}$ and $R^{18b}$ can be taken together to form a substituted or unsubstituted ring having from 3 to 10 carbon atoms and from 0 to 3 heteroatoms chosen from oxygen, nitrogen, and sulfur;
xii) —[C($R^{21a}$)($R^{21b}$)]$_x$CN;
xiii) —[C($R^{21a}$)($R^{21b}$)]$_x$NO$_2$;
xiv) —[C($R^{21a}$)($R^{21b}$)]$_x$$R^{19}$;
xv) —[C($R^{21a}$)($R^{21b}$)]$_x$SO$_2$$R^{20}$;
  $R^{20}$ is hydrogen, hydroxyl, substituted or unsubstituted $C_1$-$C_4$ linear or branched alkyl; substituted or unsubstituted $C_6$, $C_{10}$, or $C_{1-4}$ aryl; $C_7$-$C_{15}$ alkylenearyl; $C_1$-$C_9$ substituted or unsubstituted heterocyclic; or $C_1$-$C_{11}$ substituted or unsubstituted heteroaryl;
$R^{21a}$ and $R^{21b}$ are each independently hydrogen or $C_1$-$C_4$ alkyl;
the index x is from 0 to 5.

The R units can be further substituted by one or more $R^{100}$ organic radicals. The following are non-limiting examples of $R^{100}$ organic radicals that can substitute for hydrogen atoms on an R unit:

i) $C_1$-$C_{12}$ linear, branched, or cyclic alkyl, alkenyl, and alkynyl; for example, methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$);

iii) substituted or unsubstituted $C_6$ or $C_{10}$ alkylenearyl, for example, benzyl, naphthylen-1-ylmethyl, naphthylene-2-ylmethyl;

iv) substituted or unsubstituted $C_1$-$C_9$ heterocyclic rings; as described herein below;

v) substituted or unsubstituted $C_1$-$C_9$ heteroaryl rings; as described herein below;

vi) —$(CR^{102a}R^{102b})_zOR^{101}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vii) —$(CR^{102a}R^{102b})_zC(O)R^{101}$; for example, —$COCH_3$, —$CH_2COCH_3$, —$OCH_2CH_3$, —$CH_2COCH_2CH_3$, —$COCH_2CH_2CH_3$, and —$CH_2COCH_2CH_2CH_3$;

viii) —$(CR^{102a}R^{102b})_zC(O)OR^{101}$; for example, —$CO_2CH_3$, —$CH_2CO_2CH_3$, —$CO_2CH_2CH_3$, —$CH_2CO_2CH_2CH_3$, —$CO_2CH_2CH_3$, and —$CH_2CO_2CH_2CH_3$;

ix) —$(CR^{102a}R^{102b})_zC(O)N(R^{101})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

x) —$(CR^{102a}R^{102b})_zN(R^{101})_2$; for example, —$NH_2$, —$CH_2NH_2$, —$NHCH_3$, —$N(CH_3)_2$, —$NH(CH_2CH_3)$, —$CH_2NHCH_3$, —$CH_2N(CH_3)_2$, and —$CH_2NH(CH_2CH_3)$;

xi) halogen; —F, —Cl, —Br, and —I;

xii) —$(CR^{102a}R^{102b})_zCN$;

xiii) —$(CR^{102a}R^{102b})_zNO_2$;

xiv) —$CH_jX_k$; wherein X is halogen, j is from 0 to 2, j+k=3; for example, —$CH_2F$, —$CHF_2$, —$CF_3$, —$CCl_3$, or —$CBr_3$;

xv) —$(CR^{102a}R^{102b})_zSR^{101}$; for example, —SH, —$CH_2SH$, —$SCH_3$, —$CH_2SCH_3$, —$SC_6H_5$, and —$CH_2SC_6H_5$;

xvi) —$(CR^{102a}R^{102b})_zSO_2R^{101}$; for example, —$SO_2H$, —$CH_2SO_2H$, —$SO_2CH_3$, —$CH_2SO_2CH_3$, —$SO_2C_6H_5$, —$CH_2SO_2C_6H_5$, —$SO_2$[heterocyclic], —$SO_2$[heteroaryl]; and xvii) —$(CR^{102a}R^{102b})_zSO_3R^{101}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{101}$ is independently hydrogen, substituted or unsubstituted $C_1$-$C_4$ linear, branched, or cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or branched alkyl; the index z is from 0 to 4.

The following $R^{100}$ organic radicals can be substituted by one or more $R^{200}$ organic radicals:

i) $C_1$-$C_{12}$ linear, branched, or cyclic alkyl, alkenyl, and alkynyl; for example, methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$);

iii) substituted or unsubstituted $C_1$-$C_9$ heterocyclic rings; as described herein below; and iv) substituted or unsubstituted $C_1$-$C_9$ heteroaryl rings; as described herein below.

$R^{200}$ organic radicals can be one or more substitutions for hydrogen on the above $R^{100}$ organic radicals. $R^{200}$ organic radicals are each independently chosen from:

i) $C_1$-$C_4$ alkyl, alkenyl, alkynyl, alkoxy, alkenyloxy, alkynyloxy;

ii) phenyl, benzyl, or naphthyl;

iii) —OH;

iv) —$NH_2$, —$NHCH_3$, —$N(CH_3)_2$, —$NH(CH_2CH_3)$, or —$N(CH_2CH_3)_2$;

v) —F, —Cl, —Br, or —I;

vi) —CN;

vii) —$NO_2$;

viii) —SH;

ix) —$CO_2CH_3$, —$CO_2CH_2CH_3$, —$CO_2CH_2CH_2CH_3$, or —$CO_2C_6H_5$;

x) —$CH_2F$, —$CHF_2$, or —$CF_3$;

xi) —$SO_2CH_3$, —$SO_2CH_2CH_3$, —$SO_2CH_2CH_2CH_3$, or —$SO_3C_6H_5$; and xii) —$SO_3H$, —$SO_3CH_3$, —$SO_3C_6H_5$, or —$CH_2SO_3C_6H_5$.

$R^{100}$ organic radicals can comprise the following heteroaryl and heterocyclic rings. The following rings are defined by the number of carbon atoms in the ring system, for example, pyrrolyl is a $C_4$ heteroaryl ring, imidazolyl is a $C_3$ heteroaryl ring, and the like. The following are non-limiting examples of $R^{100}$ $C_1$-$C_9$ heteroaryl rings that can substitute for hydrogen on an R unit:

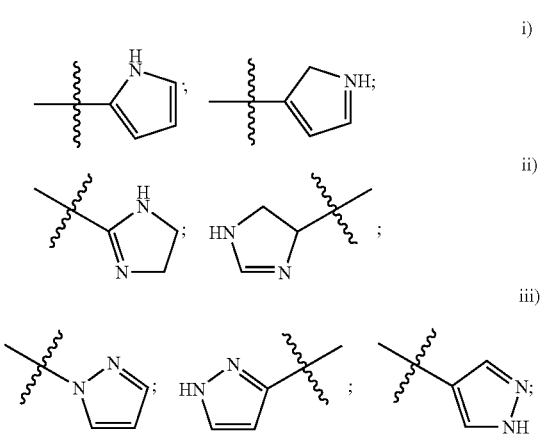

-continued
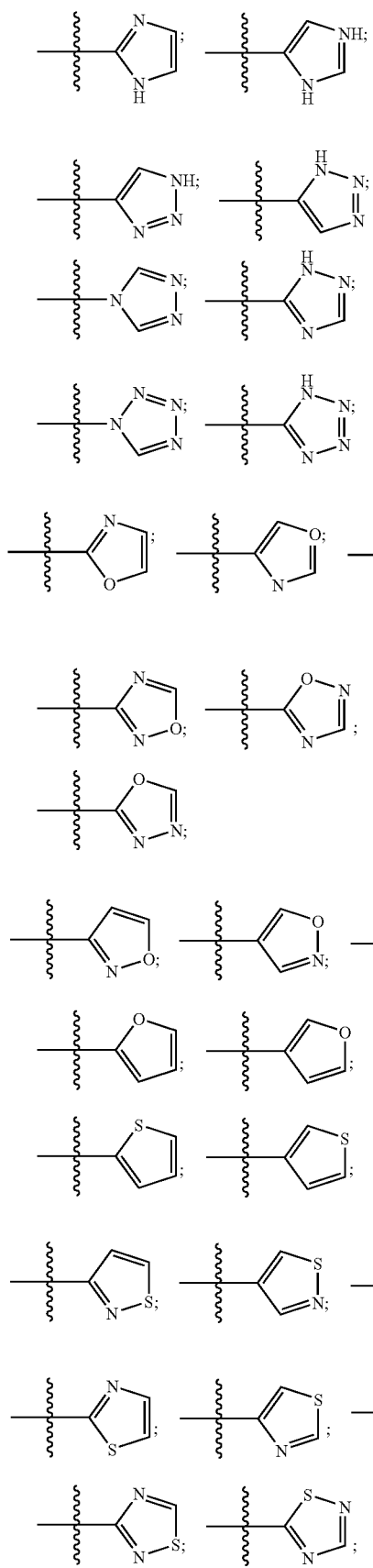
-continued
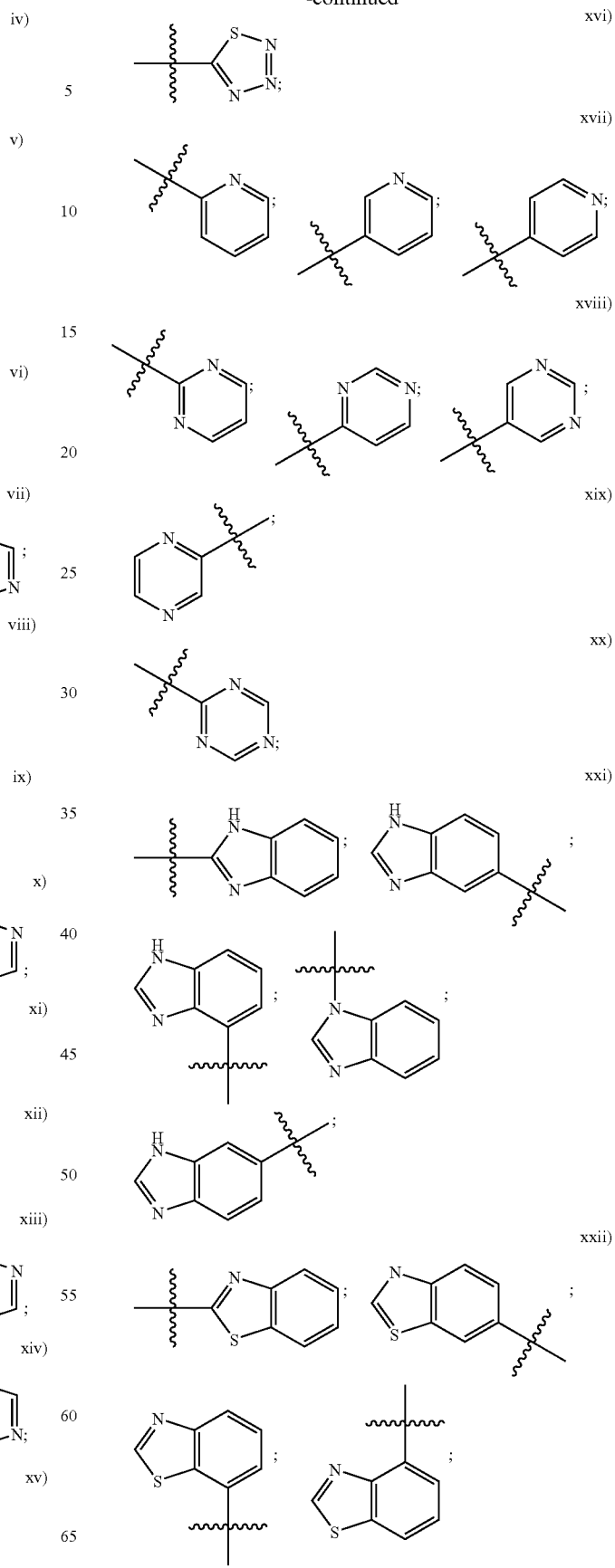

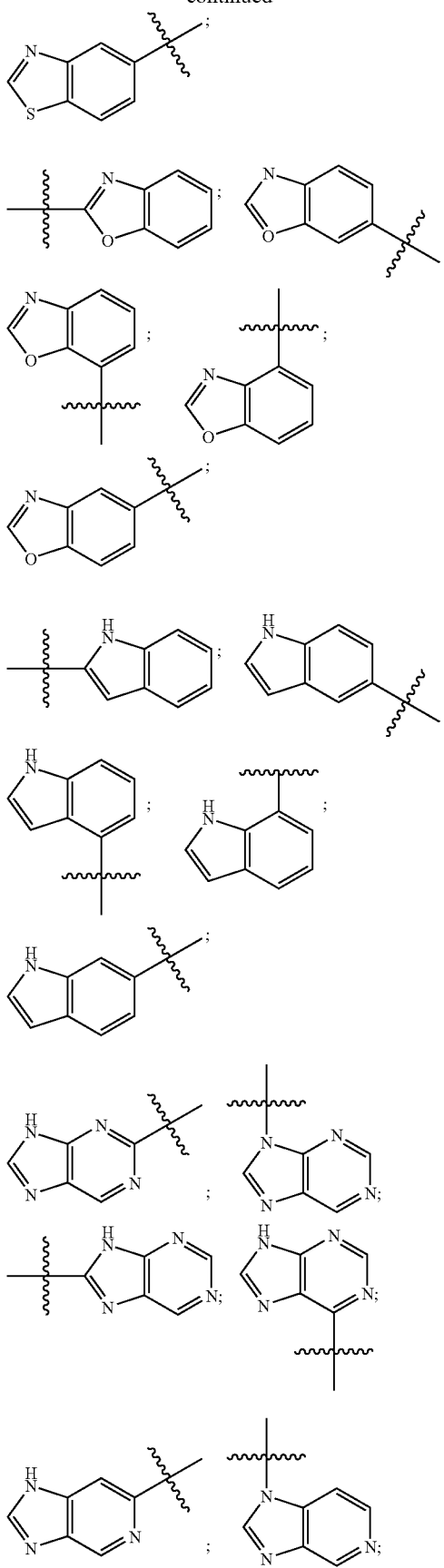
xxiii)
xxiv)
xxv)
xxvi)
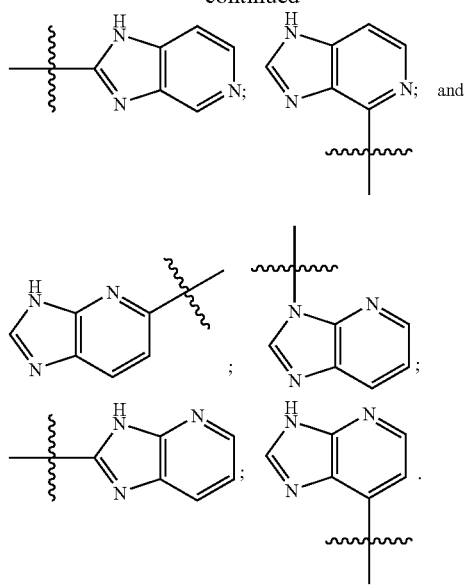
xxvii)
The following are non-limiting examples of $R^{100}$ $C_1$-$C_9$ heterocyclic rings that can substitute for hydrogen on an R unit:
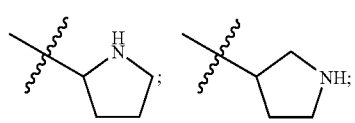
i)
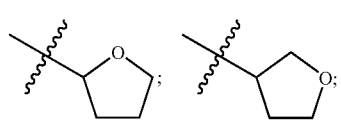
ii)
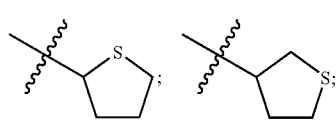
iii)
iv)
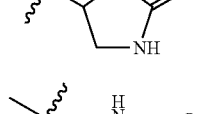
v)
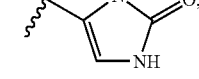
vi)

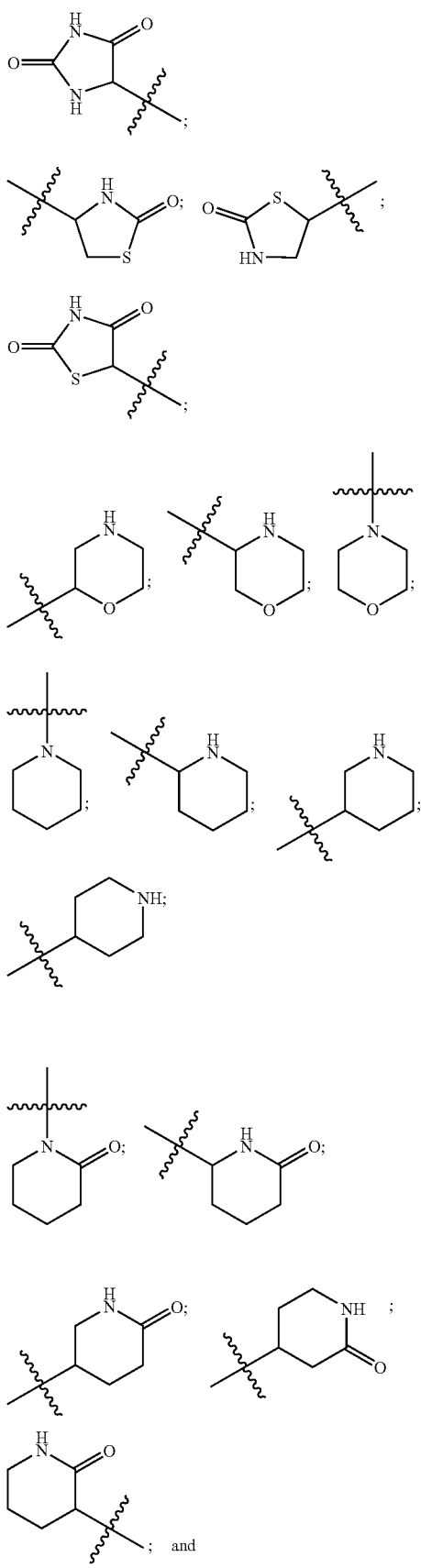
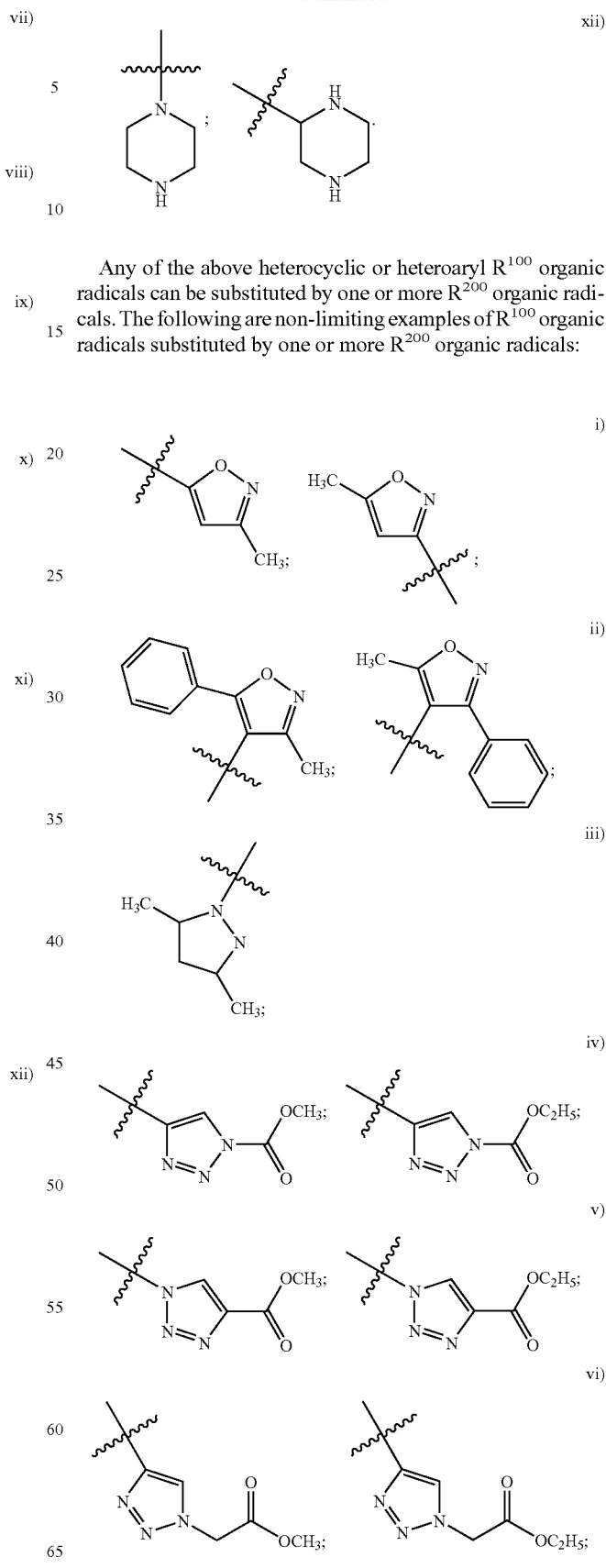
Any of the above heterocyclic or heteroaryl $R^{100}$ organic radicals can be substituted by one or more $R^{200}$ organic radicals. The following are non-limiting examples of $R^{100}$ organic radicals substituted by one or more $R^{200}$ organic radicals:

vii)

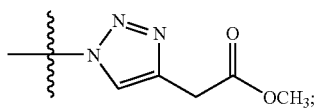

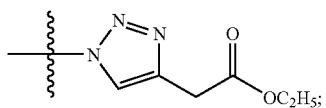

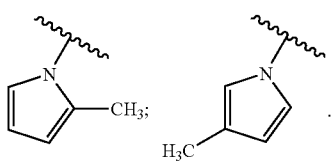

One example of A units according to the present disclosure includes units having the formula:

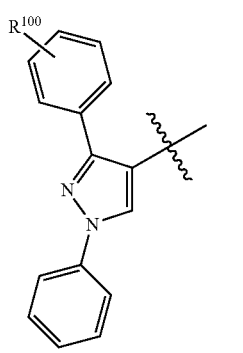

wherein $R^{100}$ is chosen from $C_1$-$C_4$ alkyl, $C_1$-$C_4$ alkoxy, phenyl, phenyloxy, benzyl, benzyloxy, that can be further substituted by one or more $R^{200}$ organic radicals. Examples include 3-(4-methylphenyl)-1-phenyl-1H-pyrazol-4-yl, 3-(4-methoxy-phenyl)-1-phenyl-1H-pyrazol-4-yl, and 3-(4-chlorophenyl)-1-phenyl-1H-pyrazol-4-yl having the formula:

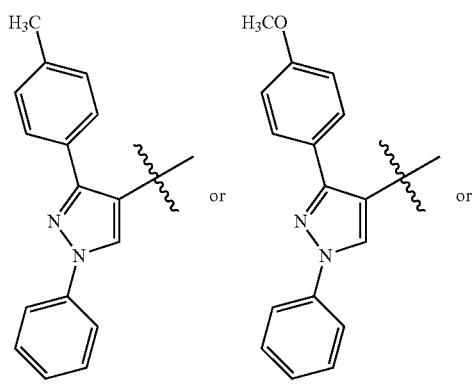

viii)

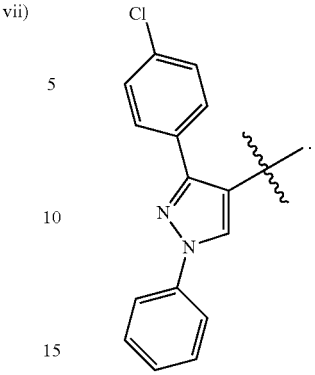

Further examples of A units include 3-[4-(benzyloxy)phenyl]-1-phenyl-1H-pyrazol-4-yl, 3-[4-(4-chlorobenzyloxy)phenyl]-1-phenyl-1H-pyrazol-4-yl, and 3-[4-(2-fluorobenzyloxy)phenyl]-1-phenyl-1H-pyrazol-4-yl having the formulae:

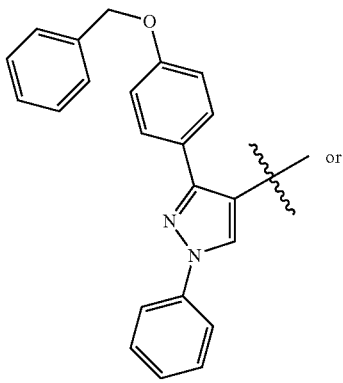

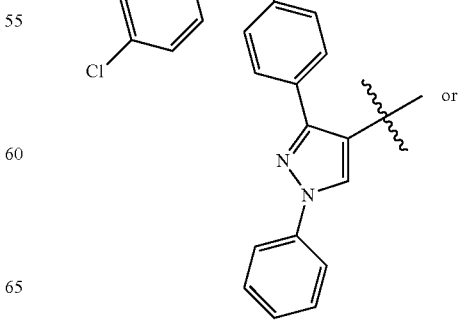

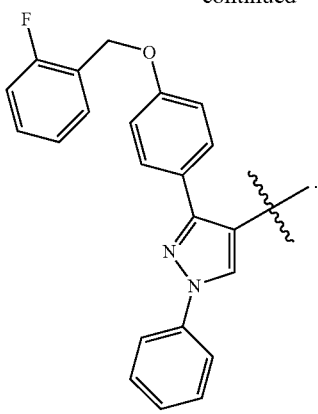

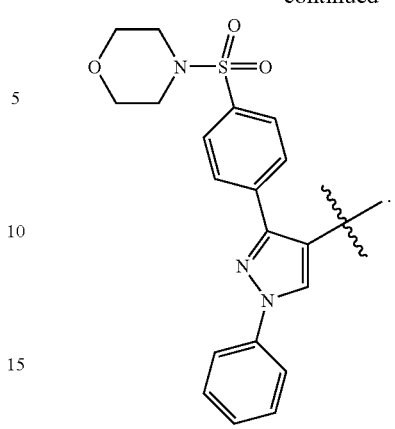

Further examples of these A units include R units that have one or more hydrogen atoms substituted by a $R^{100}$ organic radical having the formula —$SO_2R^{101}$; wherein $R^{101}$ is phenyl, phenyl substituted by one or more $R^{200}$ organic radicals, heterocyclic, heterocyclic substituted by one or more $R^{200}$ organic radicals, heteroaryl, heteroaryl substituted by one or more $R^{200}$ organic radicals. Non-limiting examples include 1-phenyl-3-[4-(phenylsulfonyl)phenyl-1H-pyrazol-4-yl, 1-phenyl-3-[4-(piperidin-1-yl)sulfonyl]phenyl-1H-pyrazol-4-yl, and 1-phenyl-3-[4-(morpholin-4-yl)sulfonyl]phenyl-1H-pyrazol-4-yl having the formulae:

Scheme I illustrates a general procedure for the formation of the compounds disclosed herein.

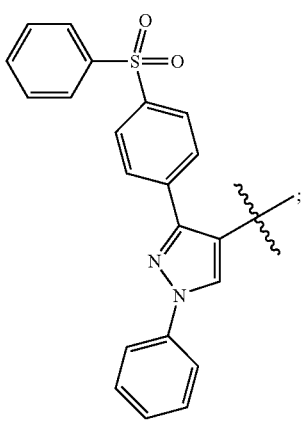

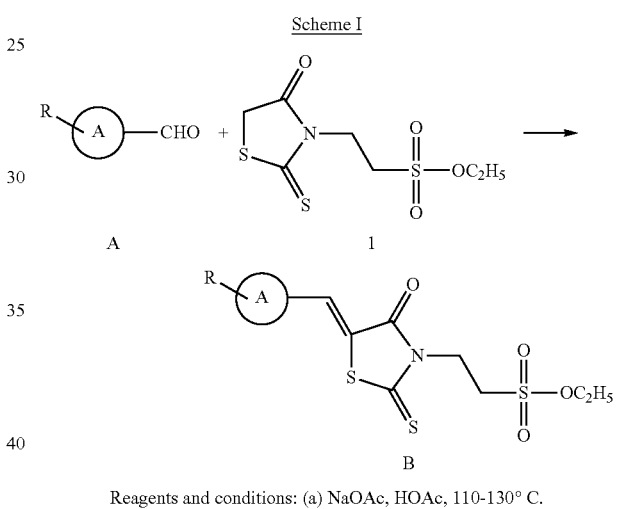

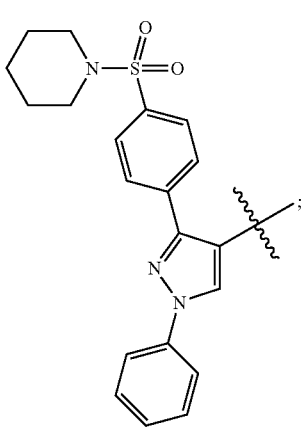

One example of the compounds disclosed herein relates to A rings that are pyrazolyl rings substituted by one or more R units. Scheme II outlines the preparation of pyrazolyl A unit intermediates.

Scheme II

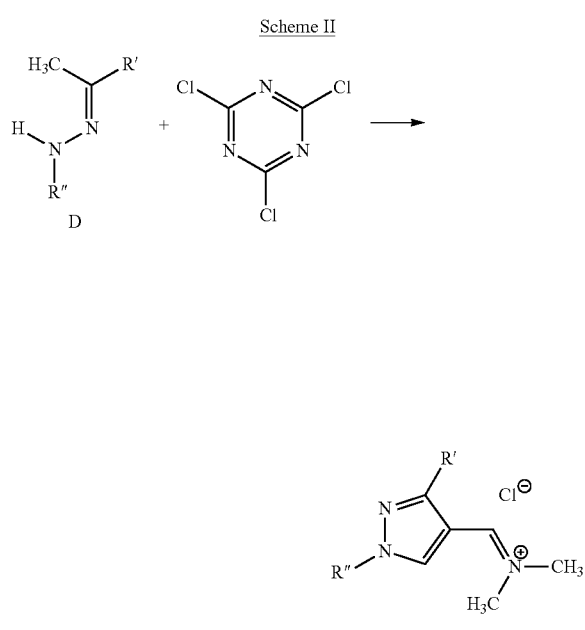

Reagents and conditions: (a) DMF; rt, 16 hr.

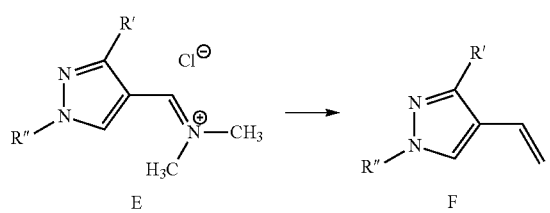

Reagents and conditions: (b) Na₂CO₃

One example of the disclosed compounds have Formula (III):

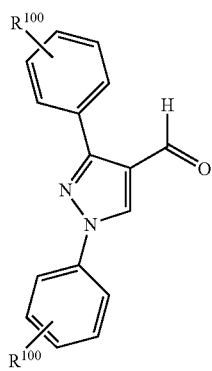

(III)

wherein $R^{100}$ can be any of the organic radicals described herein. Intermediates of Formula (III) can be made by the procedure outline in De Luca, L. et al., A Mild Procedure for the Preparation of 3-aryl-4-formylpyrazoles, *Synlett* 2004, No. 13, pp 2299-2302, included herein by reference in its entirety as outlined below in Example 1.

EXAMPLE 1

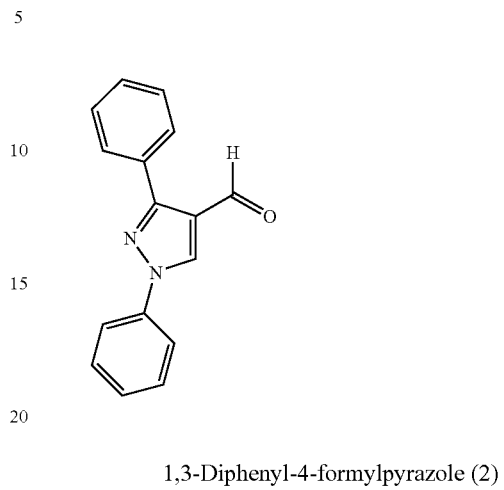

1,3-Diphenyl-4-formylpyrazole (2)

2,4,6-Trichloro[1,3,5]triazine (1.83 g, 10.0 mmol) is added to DMF (2 mL), and maintained at 25° C. After the formation of a white solid, the reaction is monitored (TLC) until complete disappearance of the triazine. 1-Phenyl-2-(1-phenylethylidene)-hydrazine (1.0 g, 5.0 mmol) in DMF (15 mL) is added. After the addition, the mixture is then stirred at room temperature and monitored for completion (TLC) after which a 15% solution of Na₂CO₃ (20 mL) is added. The organic phase is extracted twice with 15 mL of diethyl ether. The organic layer is then dried (Na₂SO₄) and the solvent is removed in vacuo to afford the desired product. Yields of approximately 1.12 g (90%) of this product can be expected when the reaction is conducted on this scale. Mp 145° C.

However, each of the phenyl rings of compound 2 can be substituted by one or more $R^{100}$ organic radicals as described herein.

Scheme III outlines the preparation of ethyl 2-(4-oxo-thioxothiazolidin-3-yl)ethanesulfonate, intermediate 1.

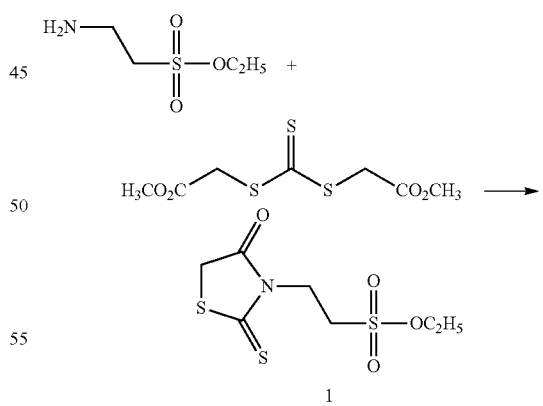

Reagents and conditions: (a) water, 95° C.

EXAMPLE 2

2-(4-oxo-thioxothiazolidin-3-yl)ethanesulfonate (1)

Ethyl 2-aminoethanesulfonate (15.3 g, 10 mmol) is suspended in water (20 mL) and heated to 95° C. until dissolved.

Bis(carboxymethyl)trithiocarbonate (25.4 g, 10 mmol) is added and the resulting solution is stirred until the disappearance of starting material. The resulting material is collected and used without further purification.

The following is a general procedure for preparing compounds having Formula (II)

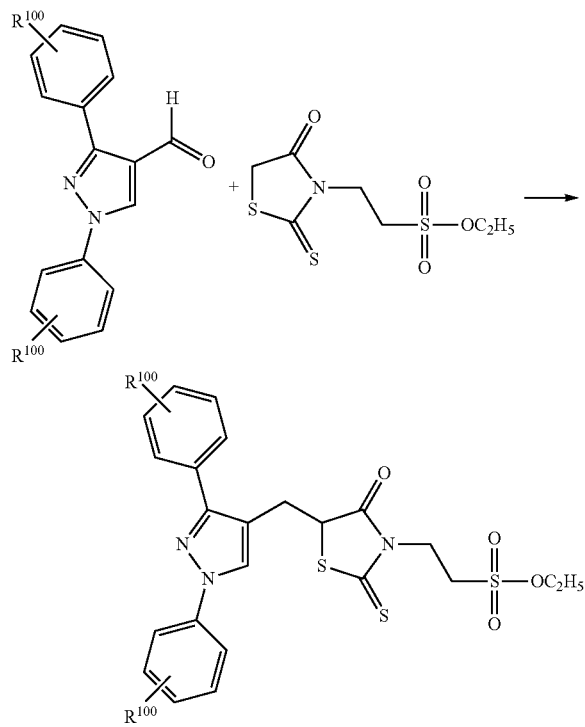

Reagents and conditions: (a) NaOAc, HOAc, 110-130° C.

Reagents and conditions: (b) HCl (aq.)

Intermediate F (1.5 equiv.) is combined with 2-(4-oxo-thioxothiazolidin-3-yl)ethanesulfonate (1 equiv.) and NaOAc (0.1 equiv.) in methanol (~10 mL per equiv. of intermediate F) and allowed to stir. Typically, after several hours the product begins to form as a solid that can be isolated by filtration. The final product can be obtained by hydrolysis of the sulfamic acid ester. After hydrolysis the product begins to form as a solid that can be isolated by filtration.

The following are non-limiting examples of compounds according to the present disclosure.

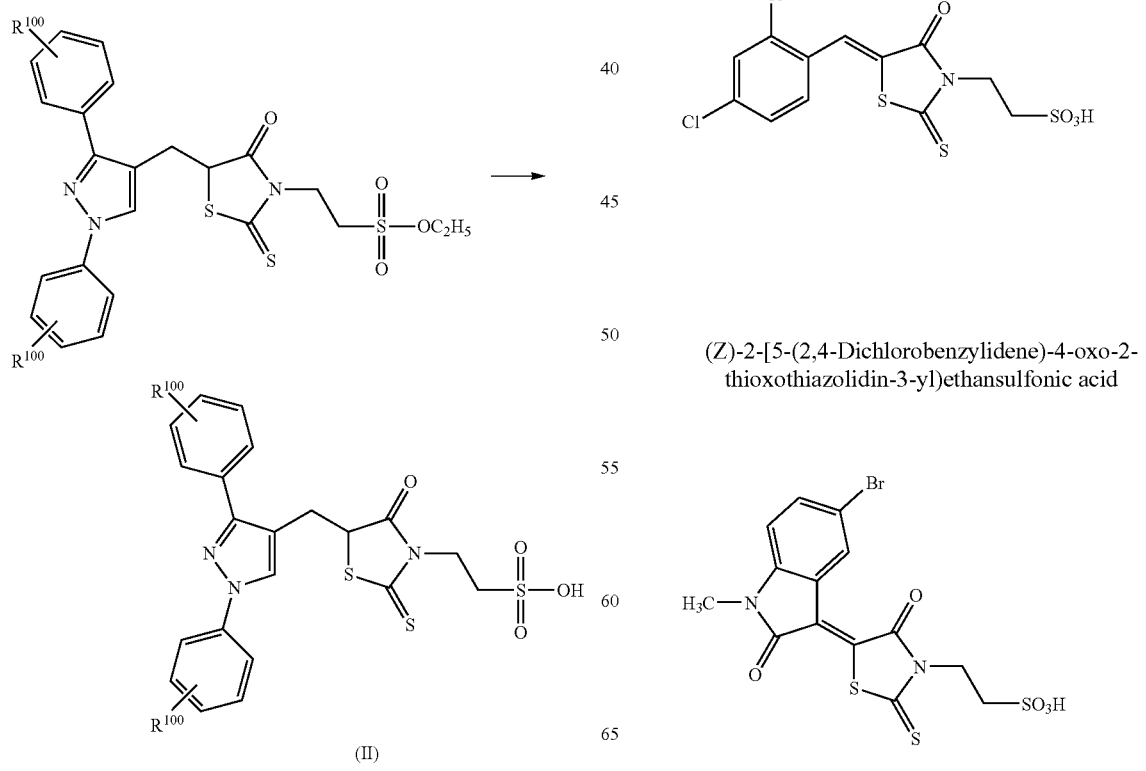

(Z)-2-[5-(3-Ethoxy-4-hydroxybenzylidene)-4-oxo-2-thioxothiazolidin-3-yl)ethansulfonic acid (Z)-2-[5-(2,4-Dichlorobenzylidene)-4-oxo-2-thioxothiazolidin-3-yl)ethansulfonic acid

45

(Z)-2-[5-(5-bromo-1-methyl-2-oxoindolin-3-ylidene)-4-oxo-2-thioxothiazolindin-3-yl]ethanesulfonic acid

46

(Z)-2-{4-oxo-5-[(1-phenyl-3-p-tolyl-1H-pyrazol-4-yl)methylene]-2-thioxothiazolidin-3-yl}ethanesulfonic acid

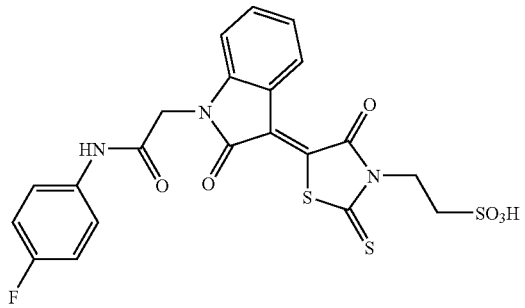

(Z)-2-(5-{1-[2-(4-fluorophenylamino)-2-oxoethyl]-2-oxoindolin-3-ylidene}-4-oxo-2-thioxothiazolindin-3-yl)ethanesulfonic acid

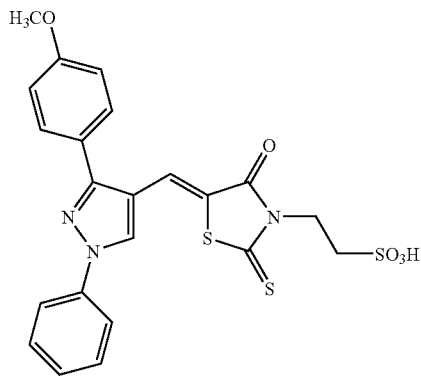

(Z)-2-(4-oxo-5-{[1-phenyl-3-(4-methoxyphenyl)-1H-pyrazol-4-yl]methylene}-2-thioxothiazolidin-3-yl)ethanesulfonic acid

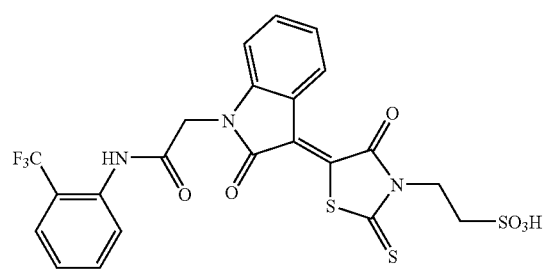

(Z)-2-[5-(1-{2-[2-(trifluoromethyl)phenylamino]-2-oxoethyl}-2-oxoindolin-3-ylidene)-4-oxo-2-thioxothiazolindin-3-yl]ethanesulfonic acid

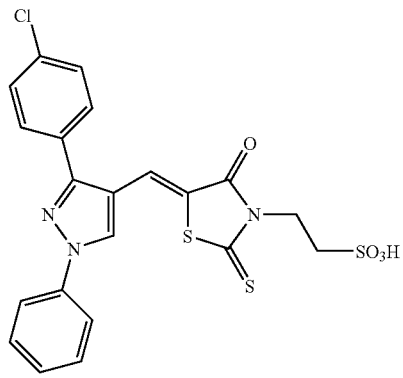

(Z)-2-(4-oxo-5-{[1-phenyl-3-(4-chlorophenyl)-1H-pyrazol-4-yl]methylene}-2-thioxothiazolidin-3-yl)ethanesulfonic acid

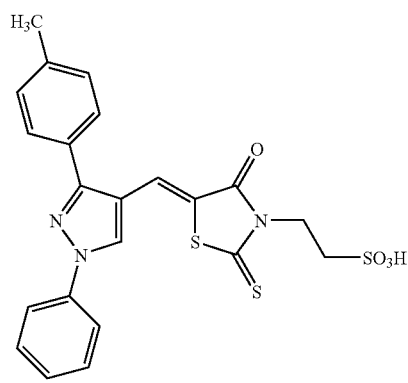

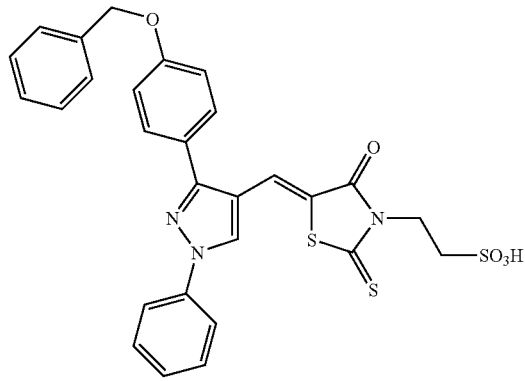

47

(Z)-2-(5-{[3-(4-benzyloxy)phenyl-1-phenyl-1H-pyrazol-4-yl]methylene-4-oxo-2-thioxothiazolidin-3-yl)ethanesulfonic acid

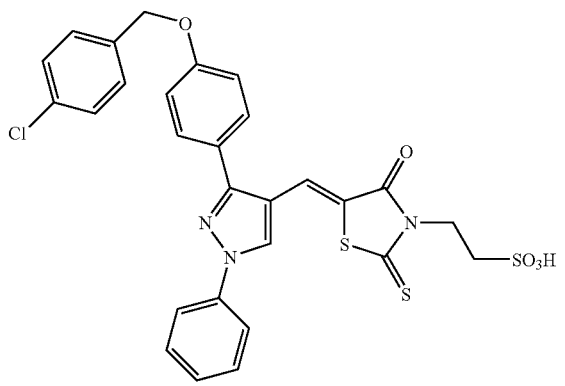

(Z)-2-[5-({3-[4-(4-chlorobenzyloxy)phenyl]-1-phenyl-1H-pyrazol-4-yl}methylene)-4-oxo-2-thioxothiazolidin-3-yl]ethane sulfonic acid

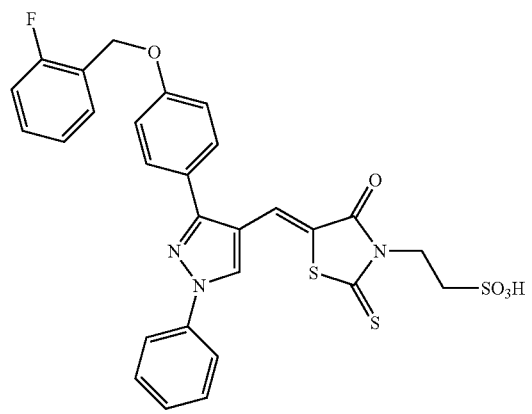

(Z)-2-[5-({3-[4-(2-fluorobenzyloxy)phenyl]-1-phenyl-1H-pyrazol-4-yl}methylene)-4-oxo-2-thioxothiazolidin-3-yl]ethane sulfonic acid

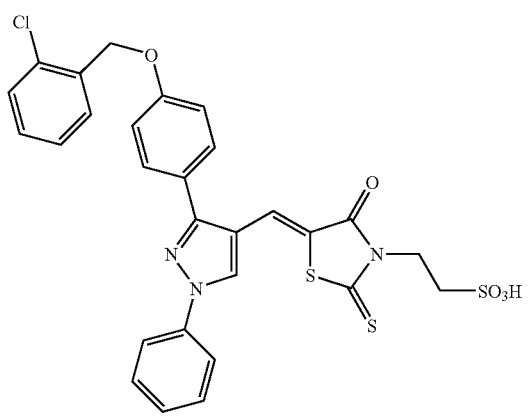

48

(Z)-2-[5-({3-[4-(2-chlorobenzyloxy)phenyl]-1-phenyl-1H-pyrazol-4-yl}methylene)-4-oxo-2-thioxothiazolidin-3-yl]ethane sulfonic acid

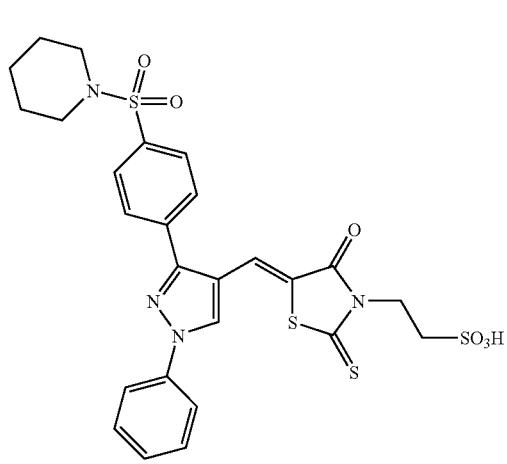

(Z)-2-[5-({3-[4-(piperidin-1-ylsulfonyl)phenyl]-1-phenyl-1H-pyrazol-4-yl}methylene)-4-oxo-2-thioxothiazolidin-3-yl]ethane sulfonic acid

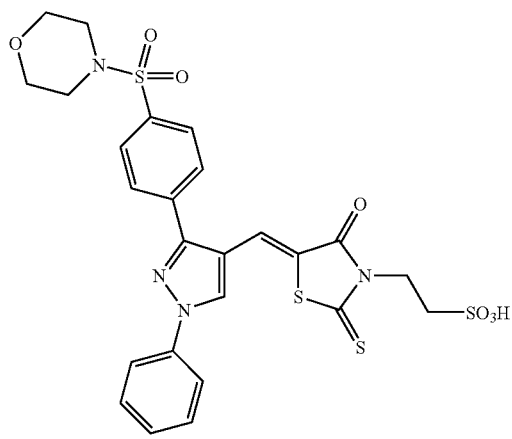

(Z)-2-[5-({3-[4morpholinosulfonyl)phenyl]-1-phenyl-1H-pyrazol-4-yl}methylene)-4-oxo-2-thioxothiazolidin-3-yl]ethane sulfonic acid Formulations The present disclosure also relates to compositions or formulations which comprise one or more *Vaccinia* H1-related (VHR) protein tyrosine phosphatase inhibitors according to the present disclosure. In general, the compositions of the present disclosure comprise:

a) an effective amount of one or more VHR protein tyrosine phosphatase inhibitors according to the present disclosure that are effective for providing treatment of cancer; and b) one or more excipients.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

Non-limiting examples of compositions according to the present disclosure include:
a) from about 0.001 mg to about 1000 mg of one or more VHR protein tyrosine phosphatase inhibitors according to the present disclosure; and
b) one or more excipients.

Another example according to the present disclosure relates to the following compositions:
a) from about 0.01 mg to about 100 mg of one or more VHR protein tyrosine phosphatase inhibitors according to the present disclosure; and
b) one or more excipients.

A further example according to the present disclosure relates to the following compositions:
a) from about 0.1 mg to about 10 mg of one or more VHR protein tyrosine phosphatase inhibitors according to the present disclosure; and
b) one or more excipients.

The term "effective amount" as used herein means "an amount of one or more VHR protein tyrosine phosphatase inhibitors, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present disclosure can be administered as frequently as necessary to achieve a therapeutic amount.

The present disclosure further relates to the use of one or more of the VHR protein tyrosine phosphatase inhibitors disclosed herein for making a medicament for treating cancer.

The present disclosure further relates to the use of one or more of the VHR protein tyrosine phosphatase inhibitors disclosed herein for making a medicament for treating a pre-leukemic disorder.

Methods

The disclosed compounds can inhibit *Vaccinia* H1-related (VHR) protein tyrosine phosphatase (PTP) that is a dual-specific Erk and Jnk phosphatase. The loss of cellular activity of this enzyme can cause cell cycle arrest in HeLa carcinoma cells. Therefore, inhibition of VHR provides a method for stopping the growth of cancer cells without having a detrimental effect on normal cells.

The compounds of the present disclosure are therefore provide a method for treating one or more cancers, for example, breast, cervical, leukemia, ovarian, hepatic, nephritic, pancreatic, brain, and lung. In addition, inhibition of VHR provides a method for treating pre-leukemic conditions.

Procedures

The PTP-catalyzed hydrolysis of 6,8-difluoro-4-methylumbelliferyl phosphate (DiFMUP) in the presence of the test compound is assayed at 30° C. in a 60 µL 96 well format reaction system in 0.15 M Bis-Tris, pH 6.0 assay buffer having an ionic strength of 150 mM (adjusted with NaCl) and containing 1 mM dithiotreitol and 5% DMSO. At various concentrations of the compound, the initial rate at fixed DiFMUP concentration (equal to the corresponding $K_m$ value for each PTP) was determined using a FLx800 micro plate reader (Bio-Tek Instruments, Inc.), an excitation wave length of 360 nm and measuring the emission of the fluorescent reaction product 6,8-difluoro-7-hydroxy-4-methylcoumarin (DiFMU) at 460 nm. The nonenzymatic hydrolysis of the substrate was corrected by measuring the control without addition of enzyme. The $IC_{50}$ value was determined by plotting the relative activity versus inhibitor concentrations and fitting to Equation 1 using the software GraphPad Prism™ (GraphPad Software, Inc.).

$$\frac{V_i}{V_0} = \frac{IC_{50}}{IC_{50} + [I]} \qquad \text{Eq. 1}$$

In this case, $V_i$, is the reaction velocity when the inhibitor concentration is [I], $V_0$ is the reaction velocity with no inhibitor and $IC_{50}=K_i+K_i[S]/K_m$.

Using the same format and buffer system as for $IC_5$ measurements, the enzyme was preincubated with various fixed concentrations of inhibitors for 10 minutes. The reaction was initiated by addition of various concentrations of DiFMUP (ranging from 0.2 to 10 $k_m$) to the reaction mixture. The initial rate was determined using a FLx800 micro plate reader (Bio-Tek Instruments, Inc.), and exitation wave length of 360 nm and measuring the emission of the fluorescent reaction product DiFMU at 460 nm. The nonenzymatic hydrolysis of the substrate was corrected by measuring the control without addition of enzyme. The inhibition constant and inhibition pattern was evaluated by fitting the data to the Michaelis-Menten equations for either competitive, uncompetitive or mixed inhibition, using nonlinear regression and the program GraphPad Prism™.

Jurkat T leukemia cells were kept at logarithmic growth in RPMI 1640 medium supplemented with 10% fetal calf serum, 2 mM L-glutamine, 1 mM sodium pyruvate, nonessential amino acids and 100 units/mL each of penicillin G and streptomycin. For TCR and CD28 induced tyrosine phosphorylation responses, normal T lymphocycles were incubated in ice for 15 minutes with 10 µg/mL OKT3 and anti-CD28 m Abs, washed, and incubated with a crosslinking sheep anti-mouse Ig for 15 minutes, washed and transferred to 37° C. for 5 minutes. Cells were pelleted and lysed in 20 mM Tris-HCl, pH 7.5, 150 mM NaCl, 5 mM EDTA containing 1% NP-40, 1 mM $N_3VO_4$, 10 µg/mL aprotinin and leupeptin, 100 µg/mL soybean trypsin inhibitor and 1 mM phenylmethylsulphonyl fluoride and clarified by centrifugation at 15,000 rpm for 20 minutes. Lysate was mixed with an equal volume of twice concentrated SDS sample buffer, boiled for 1 minute, and resolved by SDS PAGE.

TABLE I

| No. | Compound | ClogP | IC$_{50}$ μm |
|---|---|---|---|
| 1 | 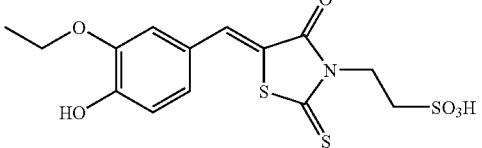<br>(Z)-2-[5-(3-Ethoxy-4-hydroxybenzylidene)-4-oxo-2-thioxothiazolidin-3-yl)ethanesulfonic acid | −0.32 | 50 |
| 2 | 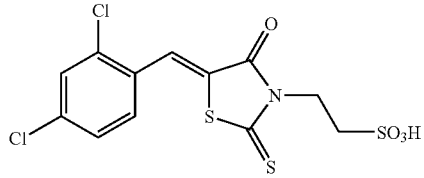<br>(Z)-2-[5-(2,3-dichlorobenzylidene)-4-oxo-2-thioxothiazolidin-3-yl)ethanesulfonic acid | 1.40 | 9.81 |
| 3 | 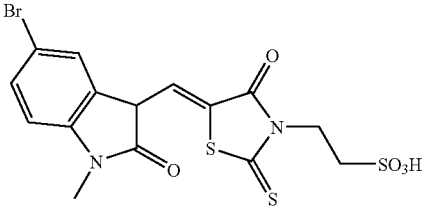<br>(Z)-2-{5-[(5-bromo-1-methyl-2-oxoindolin-3-yl)methylene]-4-oxo-thioxothiazolin-3-yl}ethanesulfonic acid | 0.61 | 32.6 |
| 4 | 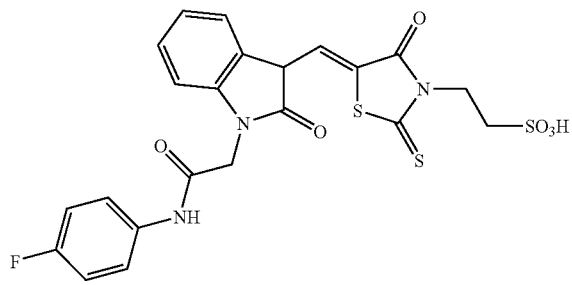<br>(Z)-2-[5-({1-[2-(4-fluorophenylamino)-2-oxoethyl]-2-oxoindolin-3-yl}methylene)-4-oxo-thioxothiazolin-3-yl]ethanesulfonic acid | 2.62 | 12.0 |
| 5 | 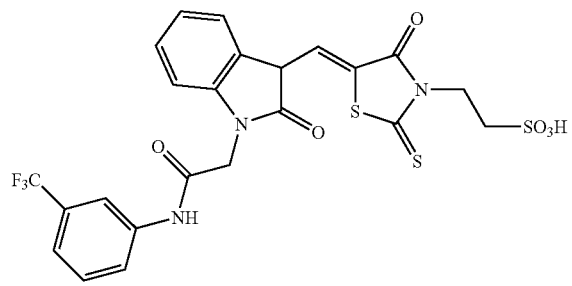<br>(Z)-2-[5-({1-[2-(3-trifluorophenylamino)-2-oxoethyl]-2-oxoindolin-3-yl}methylene)-4-oxo-thioxothiazolin-3-yl]ethanesulfonic acid | 2.1 | 4.24 |

TABLE I-continued
| No. | Compound | ClogP | IC$_{50}$ μm |
|---|---|---|---|
| 6 | 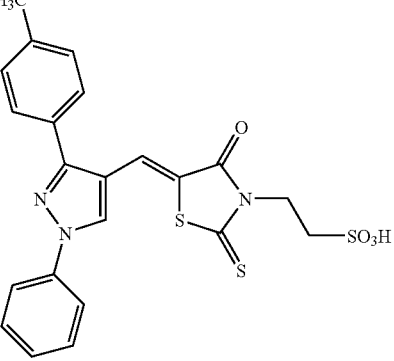 (Z)-2-{4-oxo-5-[(1-phenyl-3-p-tolyl-1H-pyrazol-4-yl)methylene]-2-thioxothiazolidin-3-yl}ethanesulfonic acid | 2.86 | 3.08 |
| 7 | 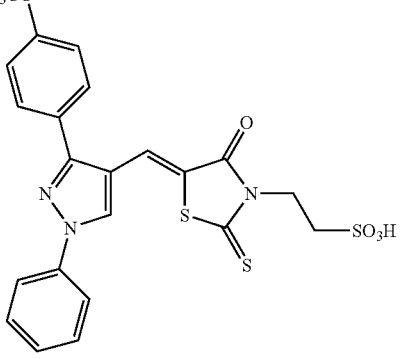 (Z)-2-(4-oxo-5-{[1-phenyl-3-(4-methoxyphenyl)-1H-pyrazol-4-yl]methylene}-2-thioxothiazolidin-3-yl)ethanesulfonic acid | 0.75 | 1.78 |
| 8 | 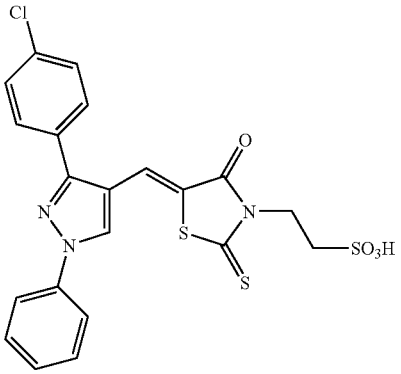 (Z)-2-(4-oxo-5-{[1-phenyl-3-(4-chlorophenyl)-1H-pyrazol-4-yl]methylene}-2-thioxothiazolidin-3-yl)ethanesulfonic acid | 1.68 | 1.80 |

TABLE I-continued

| No. | Compound | ClogP | IC$_{50}$ μm |
|---|---|---|---|
| 9 | (Z)-2-(5-{[3-(4-benzyloxy)phenyl-1-phenyl-1H-pyrazol-4-yl]methylene-4-oxo-2-thioxothiazolidin-3-yl)ethanesulfonic acid | 3.87 | 0.078 |
| 10 | (Z)-2-[5-({3-[4-(4-chlorobenzyloxy)phenyl]-1-phenyl-1H-pyrazol-4-yl}methylene)-4-oxo-2-thioxothiazolidin-3-yl]ethane sulfonic acid | 4.58 | 0.018 |
| 11 | (Z)-2-[5-({3-[4-(2-fluorobenzyloxy)phenyl]-1-phenyl-1H-pyrazol-4-yl}methylene)-4-oxo-2-thioxothiazolidin-3-yl]ethane sulfonic acid | 2.54 | 0.074 |

TABLE I-continued

| No. | Compound | ClogP | IC$_{50}$ μm |
|---|---|---|---|
| 12 | 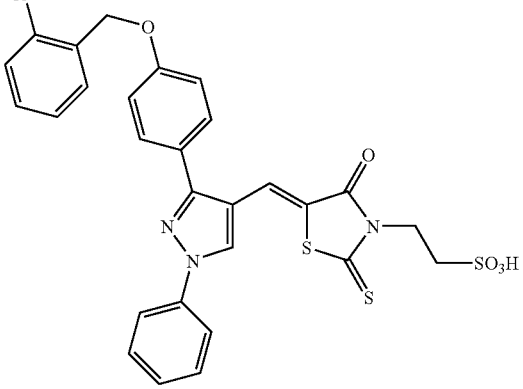<br>(Z)-2-[5-({3-[4-(2-chlorobenzyloxy)phenyl]-1-phenyl-1H-pyrazol-4-yl}methylene)-4-oxo-2-thioxothiazolidin-3-yl]ethane sulfonic acid | 1.30 | 0.071 |
| 13 | 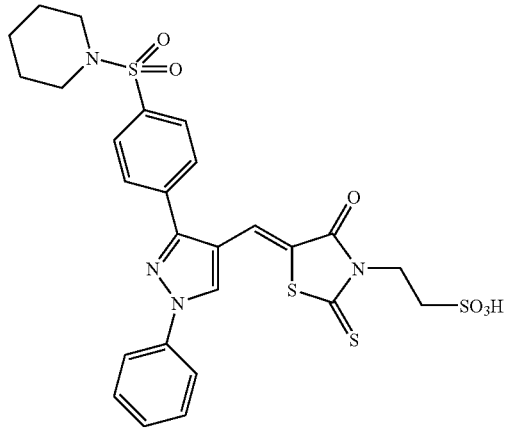<br>(Z)-2-[5-({3-[4-piperidin-1-ylsulfonyl)phenyl]-1-phenyl-1H-pyrazol-4-yl}methylene)-4-oxo-2-thioxothiazolidin-3-yl]ethane sulfonic acid | 4.01 | 0.268 |
| 14 | 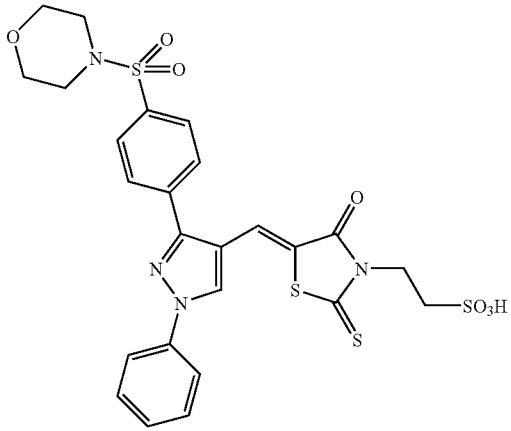<br>(Z)-2-[5-({3-[4morpholinosulfonyl)phenyl]-1-phenyl-1H-pyrazol-4-yl}methylene)-4-oxo-2-thioxothiazolidin-3-yl]ethane sulfonic acid | 4.58 | 2.44 |

Table II provides IC$_{50}$ data for compounds disclosed herein in various assays.

TABLE II

| No. | VHR | MKP-1 | HePTP | CD45 | Cdc25A | PTP1B |
|---|---|---|---|---|---|---|
| 9 | 78 | 779 | 1520 | 609 | 3436 | 1750 |
| 10 | 18 | 457 | 622 | 460 | 2448 | 456 |
| 11 | 268 | 2775 | 2380 | 1782 | >10,000 | 2190 |
| 13 | 74 | 524 | 866 | 495 | 2771 | 424 |
| 14 | 71 | 474 | 1160 | 303 | 3374 | 592 |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method of treating cancer comprising administering to a patient in need of one or more compounds, or pharmaceutically acceptable salts thereof, having the formula:

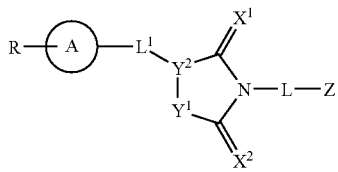

wherein A is phenyl or a heteroaryl or heterocyclic ring having from 5 to 10 ring atoms that can be further substituted by one or more R units;
each R is independently chosen from:
i) alkyl, alkenyl, or alkynyl;
ii) aryl;
iii) heterocyclic; or
iv) heteroaryl;
that can be further substituted by one or more organic radicals;
$L^1$ is a direct bond or a unit containing from 1 to 3 atoms;
$X^1$ and $X^2$ are each independently O, S, or NH;
$Y^1$ is one or two carbon atoms, a carbon and a nitrogen atom, a nitrogen atom, —O—, or —S—, wherein any of the carbon or nitrogen atoms can be further substituted by one or more organic radicals;
$Y^2$ is one or two carbon atoms, a carbon and a nitrogen atom, or a nitrogen atom, wherein any of the carbon or nitrogen atoms can be further substituted by one or more organic radicals, wherein $Y^2$ is not —CH— when $Y^1$ is —S—;
L is a linking group containing 1 to 3 carbon atoms; and
Z is a keto, sulfonic acid, sulfonamide, alkylsulphonamide, phosphonic acid, or phosphonic ester radical,
wherein the cancer is breast cancer, cervical cancer, ovarian cancer, leukemia cancer, hepatic cancer, nephritic cancer, pancreatic cancer, brain cancer, or lung cancer.

2. The method according to claim 1, wherein $Y^1$ is chosen from:
i) —C($R^{2a}$)($R^{2b}$)—;
ii) —N($R^3$)—;
iii) —C($R^{2a}$)($R^{2b}$)C($R_{2c}$)($R^{2d}$)—;
iv) —C($R^{2a}$)($R^{2b}$)N($R^3$)—;
v) —C($R^{2a}$)=N—;
vi) —O—; or
vii) —S—;
wherein $R^{2a}$, $R^{2b}$, $R^{2c}$, and $R^{2d}$ are organic radicals independently chosen from:
i) —H;
ii) $C_1$-$C_4$ substituted or unsubstituted alkyl;
iii) $C_1$-$C_4$ substituted or unsubstituted alkoxy;
iv) —OH;
v) halogen; or
vi) —CN.
$R^{2a}$ and $R^{2b}$ or $R^{2c}$ and $R^{2d}$ can be taken together to form a unit having the formula =$X^3$, wherein $X^3$ is O, S, or NH; and
$R^3$ is hydrogen or $C_1$-$C_4$ alkyl.

3. The method according to claim 2, wherein $Y^1$ is chosen from —C($R^{2a}$)($R^{2b}$)—; —N($R^3$)—; or —S—; $R^{2a}$, $R^{2b}$ and $R^3$ are each hydrogen of methyl.

4. The method according to claim 3, wherein $Y^1$ is —S—.

5. The method according to claim 1, wherein $Y^2$ is —C($R^4$)—, —N—, or $Y^2$ can form an exocyclic double bond to either $L^1$ or directly to the A ring; $R^4$ is hydrogen, methyl, or ethyl.

6. The method according to claim 5, wherein $Y^2$ is —CH—.

7. The method according to claim 5, wherein $Y^2$ forms an exocyclic double bond to $L^1$.

8. The method according to claim 5, wherein $Y^2$ forms an exocyclic double bond to the A ring.

9. The method according to claim 1, wherein $X^1$ is O or S.

10. The method according to claim 9, wherein $X^1$ is O.

11. The method according to claim 1, wherein $X^2$ is O or S.

12. The method according to claim 11, wherein $X^2$ is S.

13. The method according to claim 1 wherein the compound has the formula chosen from:

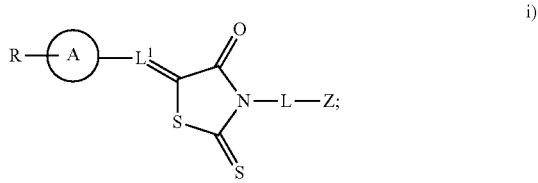

i)

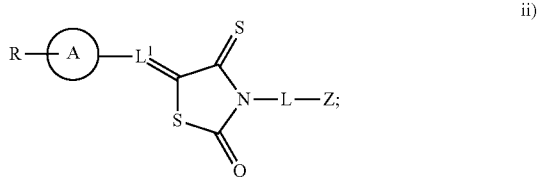

ii)

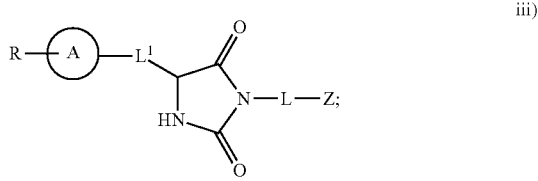

iii)

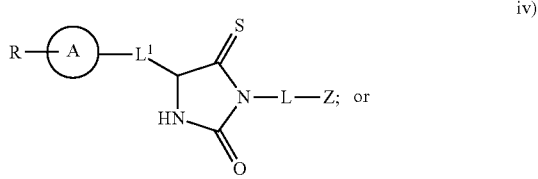

iv) or

-continued

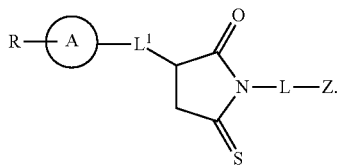
v)

14. The method according to claim 1, wherein the compound has the formula:

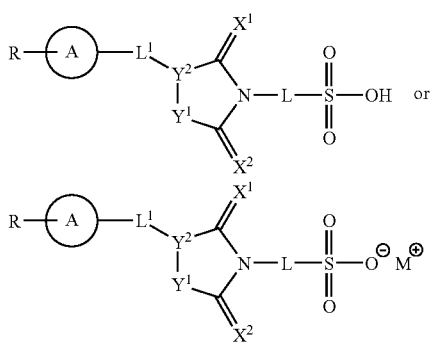

$M^+$ is a pharmaceutically acceptable cation or mixture of cations that provide electronic neutrality.

15. The method according to claim 14, wherein M is chosen from lithium, sodium, potassium, magnesium, calcium, barium, ammonium, and quaternary ammonium.

16. The method according to claim 1, wherein the compound has the formula:

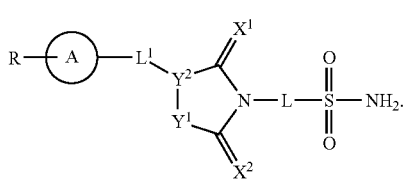

17. The method according to claim 1, wherein L units are units chosen from —CH$_2$—, —CH$_2$CH$_2$—, and —CH$_2$CH$_2$CH$_2$—.

18. The method according to claim 17, wherein L is —CH$_2$CH$_2$—.

19. The method according to claim 1, wherein A is a 5-member heteroaryl ring.

20. The method according to claim 19, wherein A is chosen from:

i)
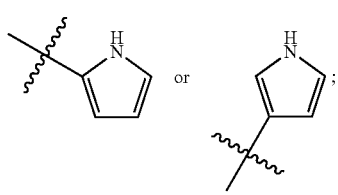

-continued ii)
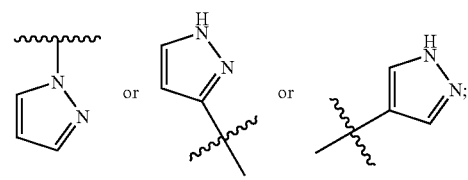

iii)
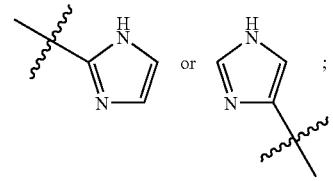

iv)
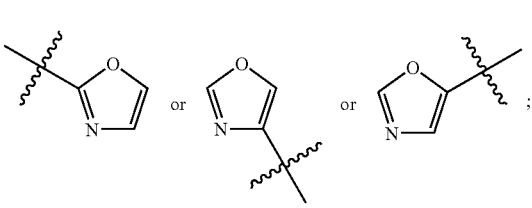

v)
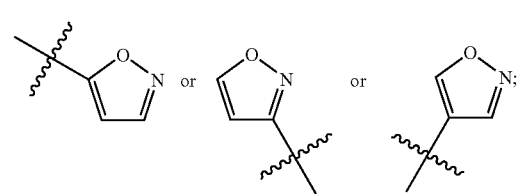

vi)
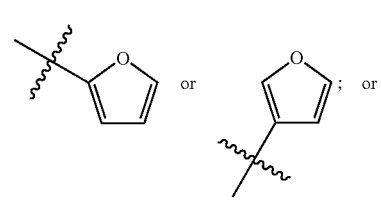

vii)
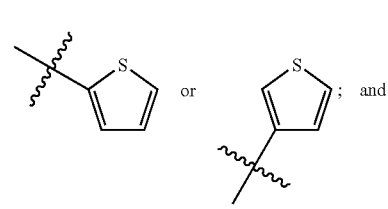

each ring can be substituted by one or more R units for hydrogen, wherein the R units are independently chosen from:
i) alkyl, alkenyl, or alkenyl;
ii) aryl;
iii) heterocyclic; or
iv) heteroaryl;
that can be further substituted by one or more organic radicals.

21. The method according to claim 20, wherein A has the formula:

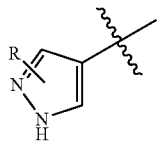

R represents from 1 to 3 substitutions for hydrogen.

22. The method according to claim 21, wherein A has the formula:

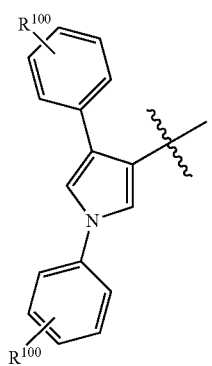

$R^{100}$ represents from 1 to 5 organic radicals that can substitute for hydrogen atoms.

23. The method according to claim 1, wherein the compound comprises an A ring that is a 9-member or 10-member heterocyclic ring chosen from:

i)

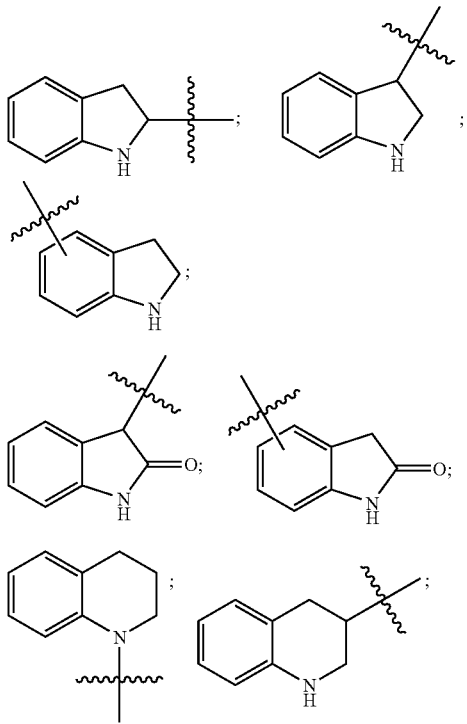

ii)

iii)

iv)

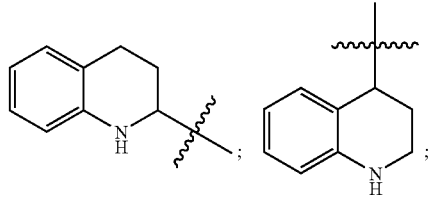

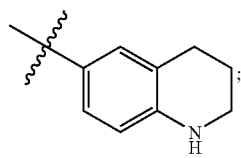

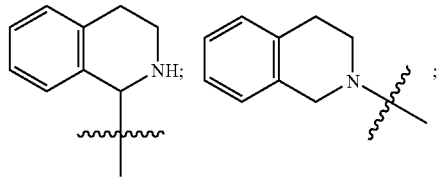

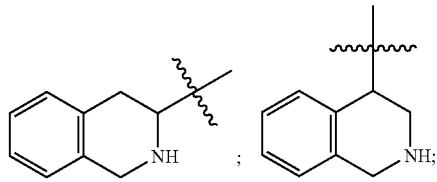

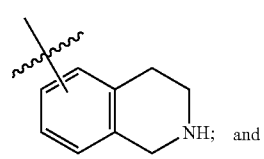

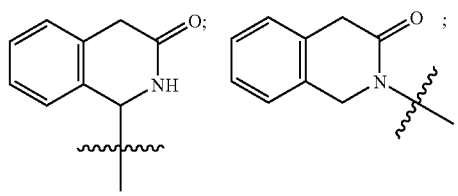

and v)

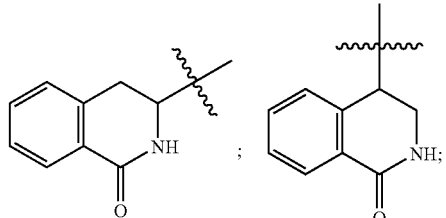

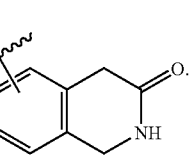

24. The method according to claim 22, the compound having the formula:

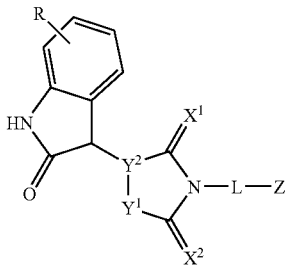

wherein R represents from 1 to 5 optional substitutions for hydrogen.

25. The method according to claim 23, wherein the compound has the formula:

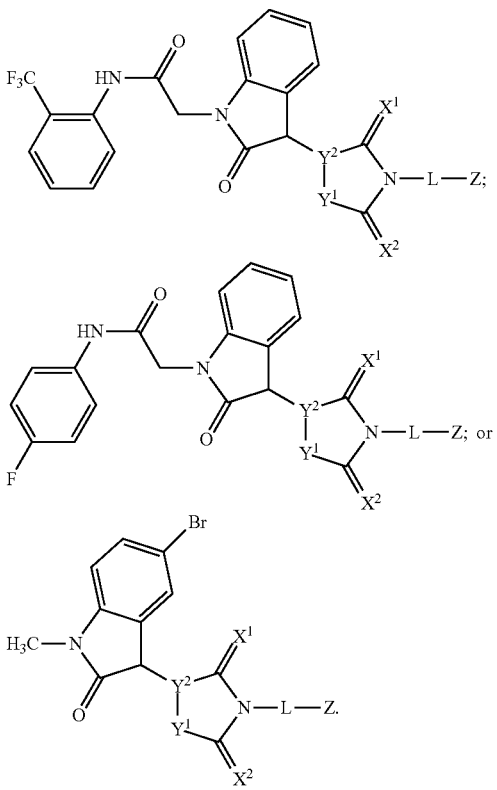

26. The method according to claim 1, wherein R is a unit chosen from:
   i) $C_1$-$C_{12}$ substituted or unsubstituted linear, branched, or cyclic alkyl;
   ii) $C_2$-$C_{12}$ substituted or unsubstituted linear, branched, or cyclic alkenyl;
   iii) $C_2$-$C_{12}$ substituted or unsubstituted linear or branched alkynyl;
   iv) $C_6$ or $C_{10}$ substituted or unsubstituted aryl;
   v) $C_1$-$C_9$ substituted or unsubstituted heterocyclic;
   vi) $C_1$-$C_{11}$ substituted or unsubstituted heteroaryl;
   vii) —[C($R^{21a}$)($R^{21b}$)]$_x$O$R^7$;

$R^7$ is chosen from:
   a) —H;
   b) $C_1$-$C_{12}$ substituted or unsubstituted linear, branched, or cyclic alkyl;
   c) $C_6$ or $C_{10}$ substituted or unsubstituted aryl or alkylenearyl;
   d) $C_1$-$C_9$ substituted or unsubstituted heterocyclic;
   e) $C_1$-$C_{11}$ substituted or unsubstituted heteroaryl;
viii) —[C($R^{21a}$)($R^{21b}$)]$_x$N($R^{8a}$)($R^{8b}$);
   $R^{8a}$ and $R^{8b}$ are each independently chosen from:
   a) —H;
   b) —O$R^9$;
      $R^9$ is hydrogen or $C_1$-$C_4$ linear alkyl;
   c) $C_1$-$C_{12}$ substituted or unsubstituted linear, branched, or cyclic alkyl;
   d) $C_6$ or $C_{10}$ substituted or unsubstituted aryl;
   e) $C_1$-$C_9$ substituted or unsubstituted heterocyclic;
   f) $C_1$-$C_{11}$ substituted or unsubstituted heteroaryl; or
   g) $R^{8a}$ and $R^{8b}$ can be taken together to form a substituted or unsubstituted ring having from 3 to 10 carbon atoms and from 0 to 3 heteroatoms chosen from oxygen, nitrogen, and sulfur;
ix) —[C($R^{21a}$)($R^{21b}$)]$_x$C(O)$R^{11}$;
   $R^{11}$ is
   a) $C_1$-$C_{12}$ substituted or unsubstituted linear, branched, or cyclic alkyl;
   b) —O$R^{12}$;
      $R^{12}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
   c) —N($R^{13a}$)($R^{13b}$);
      $R^{13a}$ and $R^{13b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{13a}$ and $R^{13b}$ can be taken together to form a substituted or unsubstituted ring having from 3 to 10 carbon atoms and from 0 to 3 heteroatoms chosen from oxygen, nitrogen, and sulfur;
x) —[C($R^{21a}$)($R^{21b}$)]$_x$OC(O)$R^{14}$;
   $R^{14}$ is
   a) $C_1$-$C_{12}$ substituted or unsubstituted linear, branched, or cyclic alkyl;
   b) —N($R^{15a}$)($R^{15b}$);
      $R^{15a}$ and $R^{15b}$ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;
xi) —[C($R_{21a}$)($R_{21b}$)]$_x$N$R^{16}$C(O)$R^{17}$;
   $R^{16}$ is:
   a) —H; or
   b) $C_1$-$C_4$ substituted or unsubstituted linear, branched, or cyclic alkyl;
   $R^{17}$ is
   a) $C_1$-$C_{12}$ substituted or unsubstituted linear, branched, or cyclic alkyl;

b) —N(R$^{18a}$)(R$^{18b}$);

R$^{18}$a and R$^{18b}$ are each independently hydrogen, C$_1$-C$_{12}$ substituted or unsubstituted linear, branched, or cyclic alkyl; C$_6$ or C$_{10}$ substituted or unsubstituted aryl; C$_1$-C$_9$ substituted or unsubstituted heterocyclic; C$_1$-C$_{11}$ substituted or unsubstituted heteroaryl; or R$^{18a}$ and R$^{18b}$ can be taken together to form a substituted or unsubstituted ring having from 3 to 10 carbon atoms and from 0 to 3 heteroatoms chosen from oxygen, nitrogen, and sulfur;

xii) —[C(R$^{21a}$)(R$^{21b}$)]$_x$CN;
xiii) —[C(R$^{21a}$)(R$^{21b}$)]$_x$NO$_2$;
xiv) —[C(R$^{21a}$)(R$^{21b}$)]$_x$R$^{19}$;
xv) —[C(R$^{21a}$)(R$^{21b}$)]$_x$SO$_2$R$^{20}$;

R$^{20}$ is hydrogen, hydroxyl, substituted or unsubstituted C$_1$-C$_4$ linear or branched alkyl; substituted or unsubstituted C$_6$, C$_{10}$, or C$_{14}$ aryl; C$_7$-C$_{15}$ alkylenearyl; C$_1$-C$_9$ substituted or unsubstituted heterocyclic; or C$_1$-C$_{11}$ substituted or unsubstituted heteroaryl;

R$^{21a}$ and R$^{21b}$ are each independently hydrogen or C$_1$-C$_4$ alkyl;

the index x is from 0 to 5.

27. The method according to claim 26, wherein R units can be substituted by one or more R$^{100}$ organic radicals each independently chosen from:
   i) C$_1$-C$_{12}$ linear, branched, or cyclic alkyl, alkenyl, and alkynyl;
   ii) substituted or unsubstituted C$_6$ or C$_{10}$ aryl;
   iii) substituted or unsubstituted C$_6$ or C$_{10}$ alkylenearyl;
   iv) substituted or unsubstituted C$_1$-C$_9$ heterocyclic rings;
   v) substituted or unsubstituted C$_1$-C$_9$ heteroaryl rings;
   vi) —(CR$^{102a}$R$^{102b}$)$_z$OR$^{101}$;
   vii) —(CR$^{102a}$R$^{102b}$)$_z$C(O)R$^{101}$;
   viii) —(CR$^{102a}$R$^{102b}$)$_z$C(O)OR$^{101}$;
   ix) —(CR$^{102a}$R$^{102b}$)$_z$C(O)N(R$^{101}$)$_2$;
   xi) halogen;
   xii) —(CR$^{102a}$R$^{102b}$)$_z$CN;
   xiii) —(CR$^{102a}$R$^{102b}$)$_z$NO$_2$;
   xiv) —CH$_j$X$_k$; wherein X is halogen, j is from 0 to 2, j+k=3;
   xv) —(CR$^{102a}$R$^{102b}$)$_z$SR$^{101}$;
   xvi) —(CR$^{102a}$R$^{102b}$)$_z$SO$_2$R$^{101}$; and
   xvii) —(CR$^{102a}$R$^{102b}$)$_z$SO$_3$R$^{101}$;
      wherein each R$^{101}$ is independently hydrogen, substituted or unsubstituted C$_1$-C$_4$ linear, branched, or cyclic alkyl, phenyl, benzyl, heterocyclic, or heteroaryl; or two R$^{101}$ units can be taken together to form a ring comprising 3-7 atoms; R$^{102a}$ and R$^{102b}$ are each independently hydrogen or C$_1$-C$_4$ linear or branched alkyl; the index z is from 0 to 4.

28. The method according to claim 27, wherein when R$^{100}$ is an organic radical chosen from:
   i) C$_1$-C$_{12}$ linear, branched, or cyclic alkyl, alkenyl, and alkynyl;
   ii) substituted or unsubstituted C$_6$ or C$_{10}$ aryl;
   iii) substituted or unsubstituted C$_1$-C$_9$ heterocyclic rings; and
   iv) substituted or unsubstituted C$_1$-C$_9$ heteroaryl rings;
   then R$^{100}$ can be further substituted by one or more substitutions for hydrogen chosen from:
   i) C$_1$-C$_4$ alkyl, alkenyl, alkynyl, alkoxy, alkenyloxy, or alkynyloxy;
   ii) phenyl, benzyl, or naphthyl;
   iii) —OH;
   iv) —NH$_2$, —NHCH$_3$, —N(CH$_3$)$_2$, —NH(CH$_2$CH$_3$), or —N(CH$_2$CH$_3$)$_2$;
   v) —F, —Cl, —Br, or —I;
   vi) —CN;
   vii) —NO$_2$;
   viii) —SH;
   ix) —CO$_2$CH$_3$, —CO$_2$CH$_2$CH$_3$, —CO$_2$CH$_2$CH$_2$CH$_3$, or —CO$_2$C$_6$H$_5$;
   x) —CH$_2$F, —CHF$_2$, or —CF$_3$;
   xi) —SO$_2$CH$_3$, —SO$_2$CH$_2$CH$_3$, —SO$_2$CH$_2$CH$_2$CH$_3$, or —SO$_3$C$_6$H$_5$; and
   xii) —SO$_3$H, —SO$_3$CH$_3$, —SO$_3$C$_6$H$_5$, or —CH$_2$SO$_3$C$_6$H$_5$.

29. A method according to claim 28, wherein the compound has the formula:

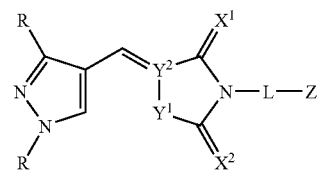

wherein R is phenyl or phenyl having from 1 to 5 hydrogen atoms substituted by one or more R$^{100}$ organic radicals.

30. The method according to claim 29, wherein R$^{100}$ is an organic radical chosen from:
   i) C$_1$-C$_4$ alkyl;
   ii) —COR$^{101}$; or
   iii) halogen;
   R$^{101}$ is hydrogen or C$_1$-C$_4$ alkyl.

31. The method according to claim 30, wherein the compound has the formula:

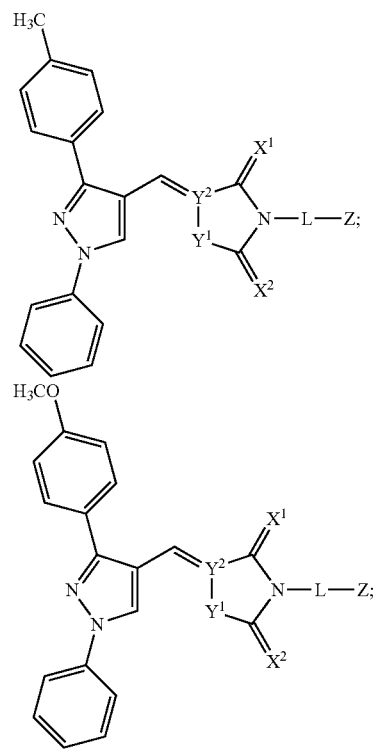

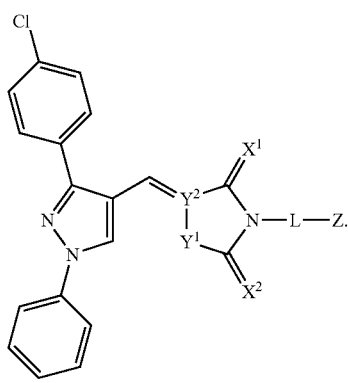

32. The method according to claim 29, wherein $R^{100}$ is an organic radical chosen from:

i) $C_1$-$C_4$ alkyl;

ii) $C_1$-$C_4$ alkoxy;

iii) phenyl;

iv) phenyloxy;

v) benzyl;

vi) benzyloxy; or vii) —$SO_2R^{101}$;

wherein the organic radicals i-vi are unsubstituted or are substituted with one or more $R_{200}$, wherein $R^{200}$ is chosen from $C_1$-$C_4$ alkyl, alkenyl, alkynyl, alkoxy, alkenyloxy, alkynyloxy, phenyl, benzyl, naphthyl, —OH, —$NH_2$, —$NHCH_3$, —$N(CH_3)_2$, —$NH(CH_2CH_3)$, —$N(CH_2CH_3)_2$, —F, —Cl, —Br, —I, —CN, —$NO_2$, —SH, —$CO_2CH_3$, —$CO_2CH_2CH_3$, —$CO_2CH_2CH_2CH_3$, —$CO_2C_6H_5$, —$CH_2F$, —$CHF_2$, or —$CF_3$, —$SO_2CH_3$, —$SO_2CH_2CH_3$, —$SO_2CH_2CH_2CH_3$, —$SO_3C_6H_5$, —$SO_3H$, —$SO_3CH_3$, —$SO_3C_6H_5$, or —$CH_2SO_3C_6H_5$; and $R^{100}$ is phenyl, benzyl, heterocyclic, or heteroaryl.

33. The method according to claim 32, wherein the compound has the formula:

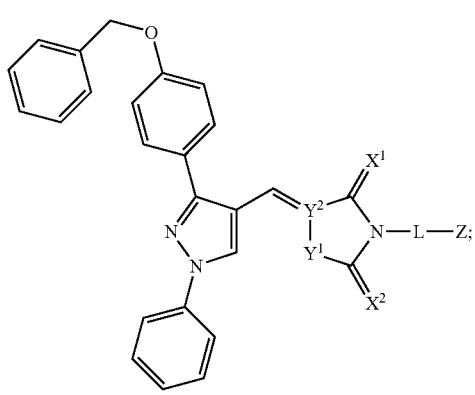

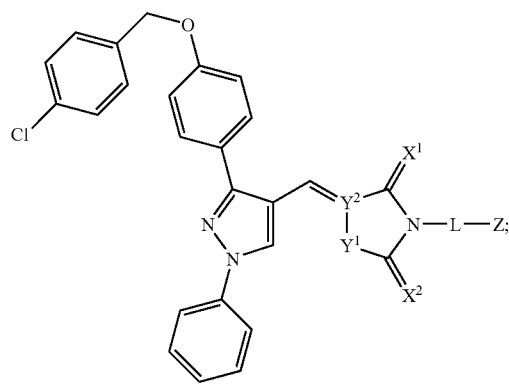

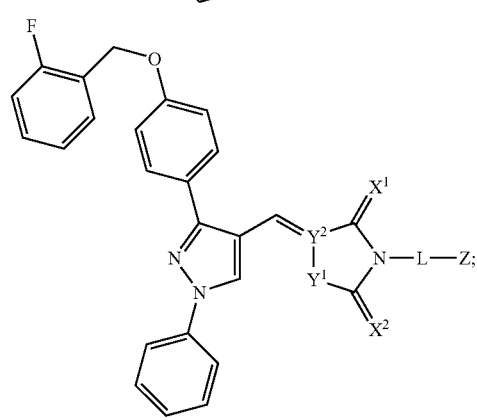

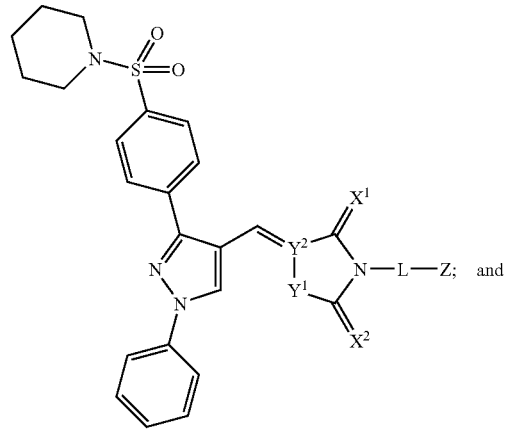

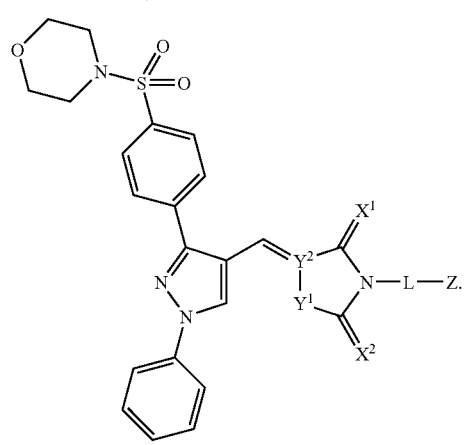

34. The method according to claim 1, wherein the compounds have the formula:
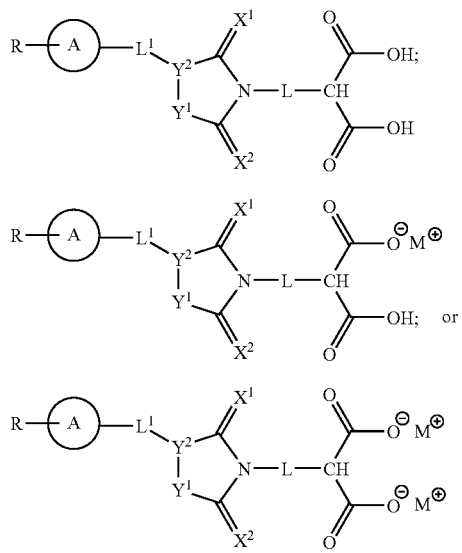
wherein M⁺ represents a pharmaceutically acceptable cation capable of providing electronic neutrality to the molecule.
35. The method according to claim 1, wherein the compounds have the formula:
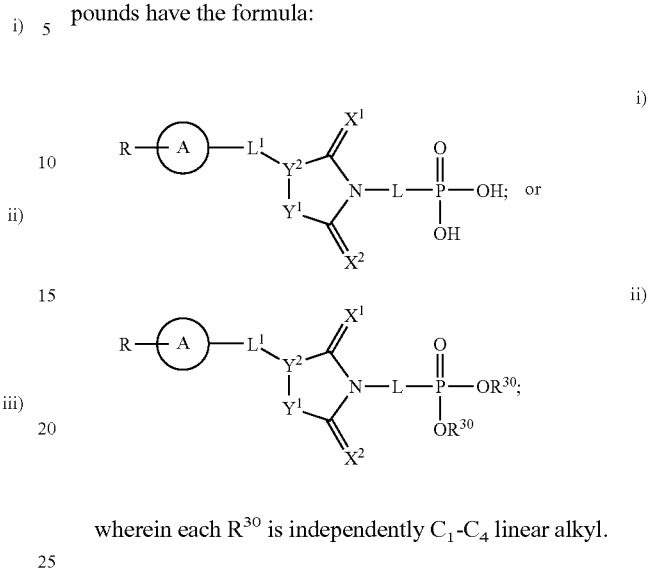
wherein each $R^{30}$ is independently $C_1$-$C_4$ linear alkyl.
* * * * *

UNITED STATES PATENT AND TRADEMARK OFFICE
CERTIFICATE OF CORRECTION

PATENT NO. : 8,188,080 B2  
APPLICATION NO. : 12/253804  
DATED : May 29, 2012  
INVENTOR(S) : Tomas Mustelin and Lutz Tautz Page 1 of 1

It is certified that error appears in the above-identified patent and that said Letters Patent is hereby corrected as shown below:

Claim 2, column 59, line 65, replace "iii) $-C(R^{2a})(R^{2b})C(R_{2c})(R^{2d})-;$" with
--iii) $-C(R^{2a})(R^{2b})C(R^{2c})(R^{2d})-;$--.
Claim 26, column 66, line 60, replace "xi) $-[C(R_{21a})(R_{21b})]_xNR^{16}C(O)R^{17};$" with
--xi) $-[C(R^{21a})(R^{21b})]_xNR^{16}C(O)R^{17};$--.

Signed and Sealed this  
Twenty-fifth Day of December, 2012

David J. Kappos  
*Director of the United States Patent and Trademark Office*